(12) United States Patent
Krolik et al.

(10) Patent No.: US 8,043,313 B2
(45) Date of Patent: Oct. 25, 2011

(54) APPARATUS AND METHODS FOR TREATING OBSTRUCTIONS WITHIN BODY LUMENS

(75) Inventors: Jeffrey A. Krolik, Campbell, CA (US);
Daryush Mirzaee, Sunnyvale, CA (US);
Gwendolyn Watanabe, Sunnyvale, CA (US); Juan Domingo, Lathrop, CA (US); James H. Dreher, Santa Monica, CA (US)

(73) Assignee: Hotspur Technologies, Inc, Mountain View, CA (US)

( * ) Notice: Subject to any disclaimer, the term of this patent is extended or adjusted under 35 U.S.C. 154(b) by 186 days.

(21) Appl. No.: 12/497,135

(22) Filed: Jul. 2, 2009

(65) Prior Publication Data
US 2010/0036410 A1    Feb. 11, 2010

Related U.S. Application Data

(60) Provisional application No. 61/078,330, filed on Jul. 3, 2008, provisional application No. 61/153,620, filed on Feb. 18, 2009, provisional application No. 61/214,667, filed on Apr. 27, 2009, provisional application No. 61/215,732, filed on May 8, 2009.

(51) Int. Cl.
*A61B 17/3207* (2006.01)
(52) U.S. Cl. ............ 606/159; 606/194; 604/99.01
(58) Field of Classification Search ........... 606/108, 606/127, 128, 159, 191–200, 113, 114; 604/99.01–99.04, 103.06–103.09; 623/1.11, 623/1.12, 1.23
See application file for complete search history.

(56) References Cited

U.S. PATENT DOCUMENTS

| | | | |
|---|---|---|---|
| 396,754 A | 1/1889 | Mayfield | |
| 4,030,503 A * | 6/1977 | Clark, III | ............ 606/159 |
| 4,273,128 A | 6/1981 | Lary | |
| 4,646,742 A | 3/1987 | Packard et al. | |
| 4,649,922 A | 3/1987 | Wiktor | |

(Continued)

FOREIGN PATENT DOCUMENTS
WO    2008117256 A3    10/2008
(Continued)

OTHER PUBLICATIONS
PCT International Search Report and Written Opinion for PCT/US2009/049639, Applicant: HotSpur Technologies, Inc., Forms PCT/ISA/220, PCT/ISA/210, and PCT/ISA/237; dated Feb. 1, 2010, 14 pages.

*Primary Examiner* — Kathleen Sonnett
(74) *Attorney, Agent, or Firm* — William A. English; Vista IP Law Group LLP

(57) ABSTRACT

An apparatus is provided that is operable in different modes to perform various functions for treating a body lumen. The apparatus includes a shaft including a proximal end, a distal end, a lumen extending therebetween, and a balloon on the distal end having an interior communicating with the lumen. The apparatus includes a valve on the distal end that selectively opens or closes an outlet communicating with the lumen. With the valve open, fluid introduced into the lumen exits the outlet into a body lumen. With the valve closed, fluid introduced into the lumen expands the balloon. The apparatus also includes an actuator for axially compressing the balloon, and a helical member extends between ends of the balloon interior that expands the balloon from a contracted condition to an expanded helical shape when the actuator is activated.

20 Claims, 22 Drawing Sheets

U.S. PATENT DOCUMENTS

| | | |
|---|---|---|
| 4,706,671 A | 11/1987 | Weinrib |
| 4,762,130 A * | 8/1988 | Fogarty et al. .................. 606/159 |
| 4,813,934 A * | 3/1989 | Engelson et al. .......... 604/99.02 |
| 4,848,342 A | 7/1989 | Kaltenbach |
| 4,848,344 A | 7/1989 | Sos et al. |
| 4,890,611 A | 1/1990 | Monfort et al. |
| 4,921,478 A | 5/1990 | Solano et al. |
| 5,011,488 A | 4/1991 | Ginsburg |
| 5,032,113 A | 7/1991 | Burns et al. |
| 5,035,705 A | 7/1991 | Burns |
| 5,059,176 A | 10/1991 | Winters |
| 5,085,636 A | 2/1992 | Burns |
| 5,100,388 A | 3/1992 | Behl et al. |
| 5,100,423 A | 3/1992 | Fearnot |
| 5,135,494 A | 8/1992 | Engelson |
| 5,141,518 A | 8/1992 | Hess et al. |
| 5,171,221 A | 12/1992 | Samson |
| 5,176,698 A | 1/1993 | Burns et al. |
| 5,192,286 A | 3/1993 | Phan et al. |
| 5,192,290 A | 3/1993 | Hilal |
| 5,192,295 A | 3/1993 | Danforth et al. |
| 5,207,229 A | 5/1993 | Winters |
| 5,211,651 A | 5/1993 | Reger et al. |
| 5,217,434 A | 6/1993 | Arney |
| 5,221,260 A | 6/1993 | Burns et al. |
| 5,259,839 A | 11/1993 | Burns |
| 5,295,959 A | 3/1994 | Gurbel et al. |
| 5,303,714 A | 4/1994 | Abele et al. |
| 5,304,198 A | 4/1994 | Samson |
| 5,308,356 A | 5/1994 | Blackshear et al. |
| 5,312,340 A | 5/1994 | Keith |
| 5,320,604 A | 6/1994 | Walker et al. |
| 5,338,295 A | 8/1994 | Cornelius et al. |
| 5,342,301 A | 8/1994 | Saab |
| 5,364,354 A | 11/1994 | Walker et al. |
| 5,372,601 A | 12/1994 | Lary |
| 5,378,238 A | 1/1995 | Peters et al. |
| 5,380,282 A | 1/1995 | Burns |
| 5,383,856 A | 1/1995 | Bersin |
| 5,385,152 A | 1/1995 | Abele et al. |
| 5,416,634 A | 5/1995 | Glynn et al. |
| 5,423,846 A | 6/1995 | Fischell |
| 5,437,632 A | 8/1995 | Engelson |
| 5,454,788 A | 10/1995 | Walker et al. |
| 5,454,789 A | 10/1995 | Burns et al. |
| 5,464,395 A | 11/1995 | Faxon et al. |
| 5,476,477 A | 12/1995 | Burns |
| 5,484,408 A | 1/1996 | Burns |
| 5,484,409 A | 1/1996 | Atkinson et al. |
| 5,527,326 A | 6/1996 | Hermann et al. |
| 5,569,195 A | 10/1996 | Saab |
| 5,569,201 A | 10/1996 | Burns |
| 5,571,122 A | 11/1996 | Kelly et al. |
| 5,624,396 A | 4/1997 | McNamara et al. |
| 5,643,298 A | 7/1997 | Nordgen et al. |
| 5,658,302 A | 8/1997 | Wicherski et al. |
| 5,662,603 A | 9/1997 | Gelbfish |
| 5,665,098 A | 9/1997 | Kelly et al. |
| 5,683,410 A | 11/1997 | Samson |
| 5,693,015 A | 12/1997 | Walker et al. |
| 5,728,067 A | 3/1998 | Enger |
| 5,749,849 A | 5/1998 | Engelson |
| 5,766,191 A | 6/1998 | Trerotola |
| 5,776,099 A | 7/1998 | Tremulis |
| 5,843,103 A | 12/1998 | Wulfman |
| 5,868,768 A | 2/1999 | Wicherski et al. |
| 5,895,398 A | 4/1999 | Wensel et al. |
| 5,906,606 A | 5/1999 | Chee et al. |
| 5,919,162 A | 7/1999 | Burns |
| 5,947,985 A | 9/1999 | Imran |
| 5,954,737 A | 9/1999 | Lee |
| 5,972,019 A | 10/1999 | Engelson et al. |
| 5,980,486 A | 11/1999 | Enger |
| 6,004,328 A | 12/1999 | Solar |
| 6,017,323 A | 1/2000 | Chee |
| 6,036,717 A | 3/2000 | Mers et al. |
| 6,050,972 A | 4/2000 | Azizi et al. |
| 6,066,158 A | 5/2000 | Engelson et al. |
| 6,090,126 A | 7/2000 | Burns |
| 6,096,055 A | 8/2000 | Samson |
| 6,129,708 A | 10/2000 | Enger |
| 6,146,396 A | 11/2000 | Konya et al. |
| 6,231,543 B1 | 5/2001 | Hedge et al. |
| 6,245,040 B1 | 6/2001 | Inderbitzen et al. |
| 6,283,950 B1 | 9/2001 | Appling |
| 6,306,124 B1 | 10/2001 | Jones et al. |
| 6,306,151 B1 | 10/2001 | Lary |
| 6,350,252 B2 | 2/2002 | Ray et al. |
| 6,440,097 B1 | 8/2002 | Kupiecki |
| 6,454,775 B1 | 9/2002 | Demarais et al. |
| 6,511,492 B1 | 1/2003 | Rosenbluth et al. |
| 6,517,273 B2 | 2/2003 | Voss et al. |
| 6,530,935 B2 | 3/2003 | Wensel et al. |
| 6,542,781 B1 | 4/2003 | Koblish et al. |
| 6,575,933 B1 * | 6/2003 | Wittenberger et al. .. 604/101.02 |
| 6,589,206 B1 | 7/2003 | Sharkawy et al. |
| 6,610,077 B1 | 8/2003 | Hancock et al. |
| 6,620,179 B2 | 9/2003 | Boock et al. |
| 6,626,861 B1 | 9/2003 | Hart et al. |
| 6,638,245 B2 | 10/2003 | Miller et al. |
| 6,660,014 B2 | 12/2003 | Demarais et al. |
| 6,666,874 B2 | 12/2003 | Heitzmann et al. |
| 6,679,860 B2 | 1/2004 | Stiger |
| 6,685,722 B1 | 2/2004 | Rosenbluth et al. |
| 6,711,444 B2 | 3/2004 | Koblish |
| 6,824,545 B2 | 11/2004 | Sepetka et al. |
| 6,945,977 B2 | 9/2005 | Demarais et al. |
| 7,004,954 B1 | 2/2006 | Voss et al. |
| 7,058,456 B2 | 6/2006 | Pierce |
| 7,070,576 B2 | 7/2006 | O'Brien et al. |
| 7,186,237 B2 | 3/2007 | Meyer et al. |
| 7,250,042 B2 | 7/2007 | Kataishi et al. |
| 7,306,617 B2 | 12/2007 | Majercak |
| 7,338,501 B2 | 3/2008 | Teague et al. |
| 7,377,931 B2 | 5/2008 | Bagaoisan |
| 7,462,183 B2 | 12/2008 | Behl et al. |
| 7,507,246 B2 | 3/2009 | McGuckin et al. |
| 7,517,352 B2 | 4/2009 | Evans et al. |
| 7,758,604 B2 | 7/2010 | Wu et al. |
| 7,879,066 B2 | 2/2011 | Desai et al. |
| 7,883,516 B2 | 2/2011 | Huang et al. |
| 2001/0031981 A1 | 10/2001 | Evans et al. |
| 2002/0133117 A1 | 9/2002 | Azizi et al. |
| 2002/0177870 A1 | 11/2002 | Sepetka et al. |
| 2003/0004542 A1 | 1/2003 | Wensel et al. |
| 2004/0133232 A1 | 7/2004 | Rosenbluth et al. |
| 2004/0243156 A1 | 12/2004 | Wu et al. |
| 2005/0131453 A1 | 6/2005 | Parodi |
| 2006/0074442 A1 | 4/2006 | Noriega et al. |
| 2006/0106407 A1 | 5/2006 | McGuckin et al. |
| 2006/0200047 A1 | 9/2006 | Galdonik et al. |
| 2007/0016244 A1 | 1/2007 | Behl et al. |
| 2007/0038225 A1 | 2/2007 | Osborne |
| 2007/0129752 A1 | 6/2007 | Webler et al. |
| 2007/0239182 A1 | 10/2007 | Glines et al. |
| 2008/0064930 A1 | 3/2008 | Turliue |
| 2008/0125798 A1 | 5/2008 | Osborne et al. |
| 2008/0177277 A1 | 7/2008 | Behl et al. |
| 2008/0200873 A1 | 8/2008 | Espinosa et al. |
| 2008/0228209 A1 | 9/2008 | DeMello et al. |
| 2008/0262487 A1 | 10/2008 | Wensel et al. |
| 2008/0269798 A1 | 10/2008 | Ramzipoor et al. |
| 2008/0306440 A1 | 12/2008 | Hirszowicz et al. |
| 2009/0018549 A1 | 1/2009 | Desai et al. |
| 2009/0018569 A1 | 1/2009 | Desai et al. |
| 2009/0076539 A1 | 3/2009 | Valaie |

FOREIGN PATENT DOCUMENTS

| | | |
|---|---|---|
| WO | 2008117257 A3 | 10/2008 |

* cited by examiner

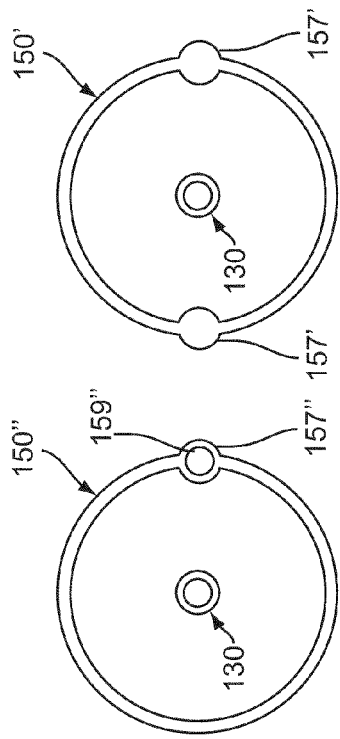
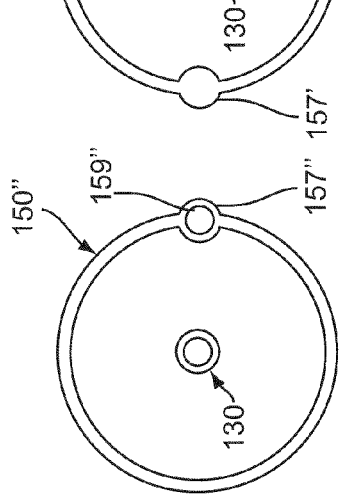
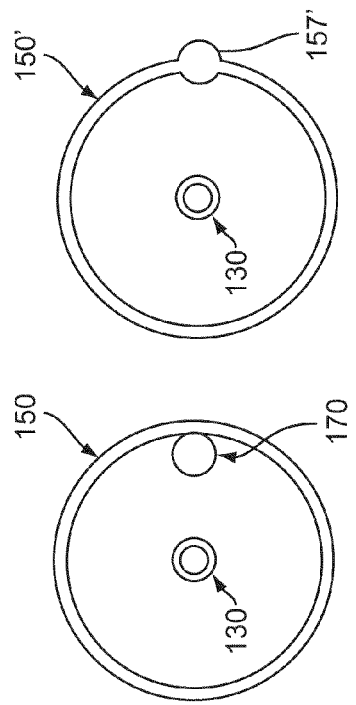
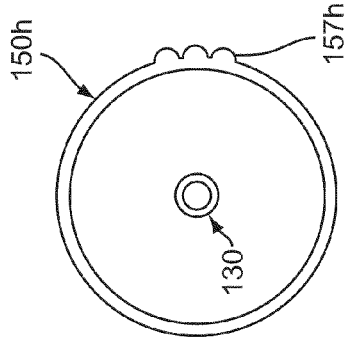
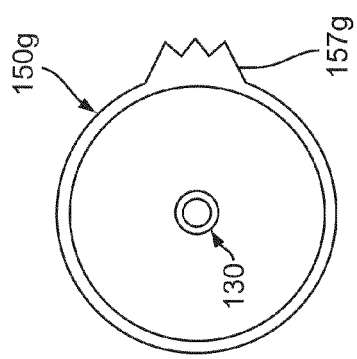
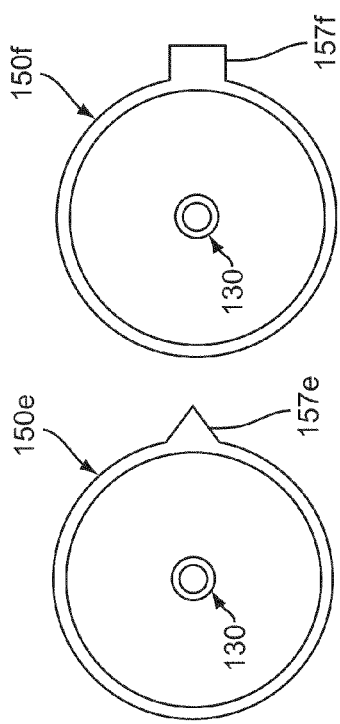

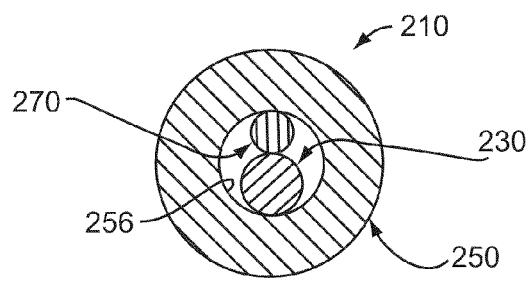
FIG. 10A
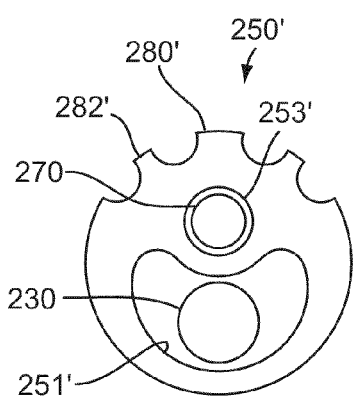   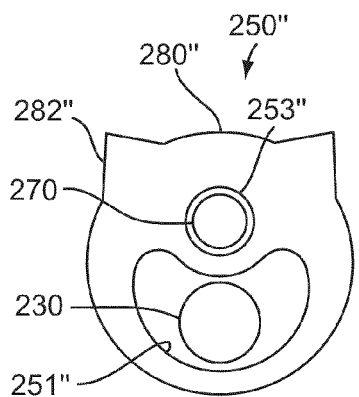   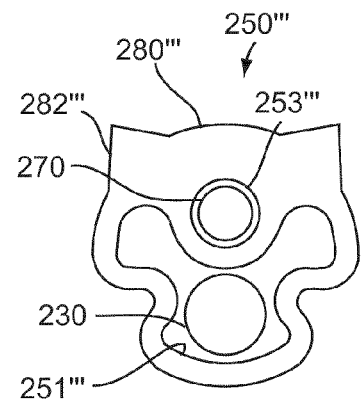
FIG. 10B       FIG. 10C       FIG. 10D

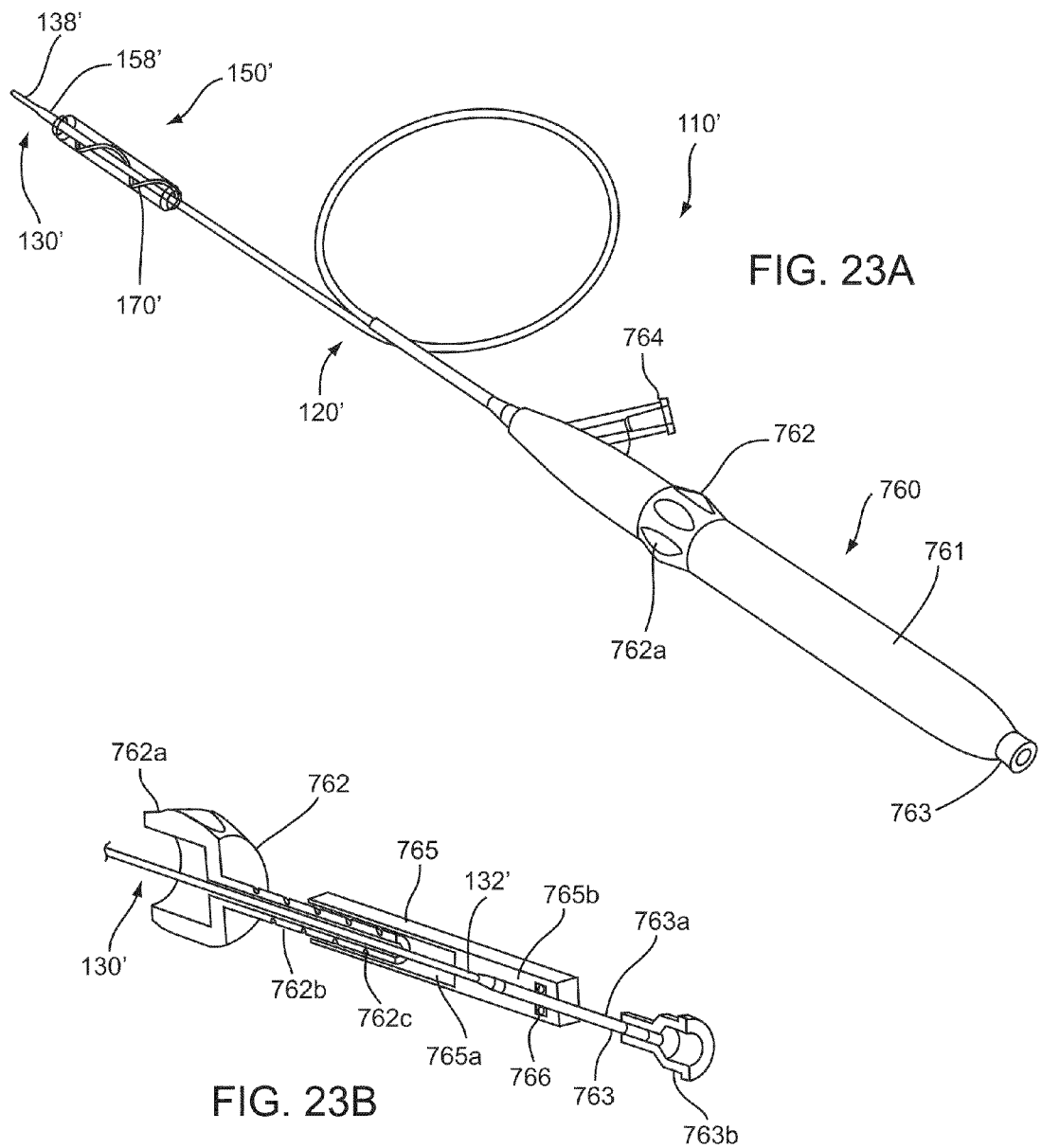

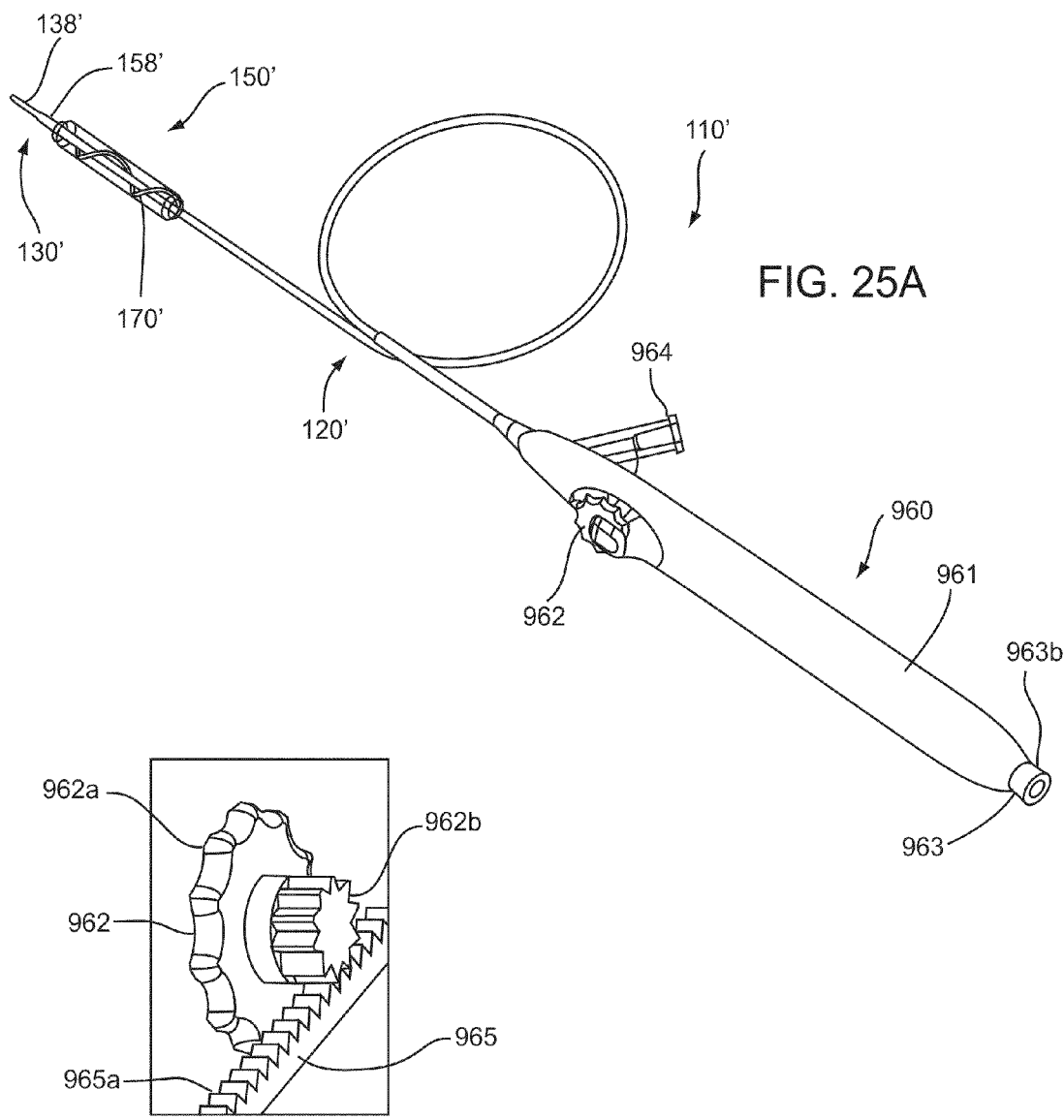

APPARATUS AND METHODS FOR TREATING OBSTRUCTIONS WITHIN BODY LUMENS

RELATED APPLICATIONS

This application claims benefit of co-pending U.S. provisional application Ser. Nos. 61/078,330, filed Jul. 3, 2008, 61/153,620, filed Feb. 18, 2009, 61/214,667, filed Apr. 27, 2009, and 61/215,732, filed May 8, 2009, the entire disclosures of which are expressly incorporated by reference herein.

FIELD OF THE INVENTION

The present invention relates generally to apparatus for treating obstructive material and/or other obstructions within a body lumen of a patient, e.g., within a tubular graft, aorto-venous fistula, blood vessel, and the like. More particularly, the present invention relates to apparatus, e.g., balloon catheters, for infusing fluids into a body lumen, for removing or otherwise capturing thrombus or other obstructive material within a body lumen, and/or for dilating a body lumen, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Accordingly, apparatus and methods for removing material from aorto-venous grafts, blood vessels, or other body lumens and/or otherwise treating body lumens would be useful.

SUMMARY

The present invention is directed to apparatus for treating a body lumen of a patient, e.g., a tubular graft, aorto-venous fistula, blood vessel, and the like. More particularly, the present invention is directed to apparatus for infusing fluids into a body lumen, for removing or otherwise capturing thrombus or other obstructive material within a body lumen, and/or for dilating a body lumen, and to methods for making and using such apparatus.

In accordance with a first embodiment, an apparatus is provided for treating a body lumen that is operable in different modes to perform various functions, e.g., possibly reducing the number of device exchanges during a procedure. For example, the apparatus may include a shaft including a proximal end, a distal end sized for introduction into a body lumen, a lumen extending therebetween, and a balloon on the distal end having an interior communicating with the lumen. The apparatus may also include a valve on the distal end of the shaft that selectively opens or closes an outlet communicating with the lumen. With the valve open, fluid introduced into the lumen may exit the outlet into a body lumen beyond the distal end. With the valve closed, fluid introduced into the lumen may expand the balloon from a contracted condition to an expanded condition, e.g., a cylindrical shape for dilating an obstruction within a body lumen or a bulbous shape for removing material within the body lumen. Optionally, the valve may include a stop that may be extended to push a distal end of the balloon, e.g., to stretch or otherwise reduce a profile of the balloon and/or otherwise facilitate introduction into a patient's body.

In addition or alternatively, the apparatus may include an actuator for axially compressing the balloon, and the balloon may be configured to expand from the contracted condition to an expanded helical shape when axially compressed. For example, the actuator may include an inner member within the shaft that is coupled to a distal end of the balloon, and a helical member may extend around the inner member within the balloon. When the inner member is directed proximally or otherwise actuated, the helical member may be compressed and consequently expand radially outwardly, thereby expanding the balloon to the expanded helical shape. The inner member may be extended distally to extend and return the balloon back towards the contracted condition, e.g., after using the balloon in the expanded helical shape to remove material within a body lumen.

In accordance with another embodiment, an apparatus is provided for treating a body lumen that includes an elongate tubular member including a proximal end, a distal end, and a first lumen extending between the proximal and distal ends; an expandable balloon including a proximal end secured to the tubular member distal end, and a distal end including an outlet, the balloon including an interior communicating with the first lumen and the balloon outlet; and an elongate member slidably disposed within the first lumen. The elongate member may include a proximal end adjacent the tubular member proximal end, and a distal end extending from the balloon outlet. The balloon and elongate member may include cooperating features providing a valve for selectively opening and closing the balloon outlet. For example, a sealing member on the distal end of the elongate member sized to be engaged with the balloon distal end to substantially seal the outlet from fluid flow.

The elongate member may be movable between a first position wherein the sealing member is spaced apart from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon.

Optionally, the apparatus may include a helical member including a first end coupled to the tubular member distal end and a second end coupled to the elongate member distal end, the helical member extending helically around the elongate member within the balloon interior. The elongate member may be movable to a third position in which the elongate member distal end is directed towards the tubular member distal end to cause the helical member to compress axially and expand radially outwardly, thereby expanding the balloon to an expanded helical shape.

In accordance with yet another embodiment, an apparatus is provided for treating a body lumen that includes an outer tubular member including a proximal end, a distal end, and a first lumen extending between the proximal and distal ends; an inner member slidably disposed within the first lumen; and an expandable balloon including a proximal end secured to the outer member distal end, an interior communicating with the first lumen and a balloon outlet. The inner member includes a distal end extending from the balloon outlet, and carrying one or more sealing members. A helical member includes a first end coupled to the outer member distal end and a second end coupled to the inner member distal end, the helical member extending helically around the inner member within the balloon interior.

The inner member may be movable relative to the outer member for deploying the balloon in multiple modes. For example, the inner member may be movable from a first position wherein the sealing member is spaced from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon. In addition or alternatively, the inner member may be movable from the first position to a third position in which the inner member distal end is directed proximally towards the outer member distal end to cause the helical member to expand radially outwardly, thereby expanding the balloon to an expanded helical shape.

In accordance with still another embodiment, an apparatus is provided for treating a body lumen that includes an outer tubular member including a first lumen extending between proximal and distal ends thereof, an inner member slidably disposed within the first lumen, and an expandable balloon comprising a proximal end secured to the outer member distal end, and a distal end coupled to a distal end of the inner member. The balloon includes an interior communicating with the first lumen such that inflation media may be delivered through the first lumen into the balloon interior for expanding the balloon radially outwardly from a contracted condition to an expanded condition, e.g., defining a cylindrical or bulbous shape. The inner member may be movable axially relative to the outer member for causing the balloon to compress axially and expand radially from the contracted condition to an expanded helical shape.

For example, the apparatus may include a helical member extending helically around the inner member within the balloon interior, and including a first end coupled to the outer member distal end and a second end coupled to the inner member. When the inner member is moved axially, the helical member may be compressed axially and expanded radially outwardly, thereby directing the balloon to the expanded helical shape.

Optionally, the inner member may include a second lumen extending between the inner member proximal and distal ends, e.g., for receiving a guidewire or other rail. Thus, the apparatus may be advanced over a guidewire loaded through the second lumen. Once the balloon is disposed within a target body lumen, the inner member may be directed to one or more of the first, second, and/or third positions, as desired, to perform various functions using the apparatus, e.g., without having to remove the apparatus and/or introduce another device into the body lumen.

In accordance with another embodiment, a method is provided for treating a body lumen of a patient using a balloon apparatus that includes an elongate shaft including a first lumen extending between proximal and distal ends thereof, and a balloon carried on the distal end of the shaft that includes an outlet and an interior communicating with the first lumen and the outlet. The distal end of the shaft may be introduced into a body lumen with the balloon in a contracted condition, and positioned relative to obstructive material within the body lumen that is to be removed. Once positioned adjacent the obstructive material, the balloon may be expanded from the contracted condition to an expanded helical shape, and the distal end of the apparatus may be directed along the body lumen with the balloon in the expanded helical shape to remove the material from the body lumen. For example, the helical shape of the balloon may enhance dislodging material adhered to a wall of the body lumen. Optionally, the balloon may include one or more features, e.g., edges, grooves, and the like, to facilitate separating adherent material from the wall of the body lumen. If desired, the balloon may be returned to the contracted condition, moved to a new location within the body lumen, and again expanded to the expanded helical shape to remove additional material within the body lumen. Once sufficient material is removed, the balloon may be returned to the contracted condition.

Before or after removing obstructive material from the body lumen, inflation media may be introduced through the first lumen into the balloon interior to expand the balloon from the contracted condition to an expanded condition, e.g., defining a substantially cylindrical shape. The balloon may be expanded to dilate an obstruction, lesion or otherwise treat a wall of the body lumen. After dilating the body lumen, the inflation media may be withdrawn from the balloon interior through the first lumen to collapse the balloon back towards the contracted condition.

If the apparatus includes a valve adjacent the balloon for opening or closing an outlet communicating with the first lumen and the balloon interior, the valve may be closed before inflating the balloon. Optionally, at any time during the procedure, the valve may be opened, e.g., to infuse fluid into the body lumen, e.g., for diagnostic and/or therapeutic purposes. After expanding the balloon one or more times, e.g., to the cylindrical shape and/or helical shape, the distal end of the apparatus may be removed from the body lumen and/or entirely from the patient's body with the balloon in the contracted condition.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 7A-7H are cross-sections of the balloon of the apparatus of FIG. 7, showing alternate constructions for integrally forming a helical member into the balloon.

FIGS. 10A-10D are cross-sectional views of alternative embodiments of balloon structures that may be provided on the apparatus of FIG. 8 to enhance removal of adherent material within a body lumen.

FIG. 23A is a perspective view of an apparatus, similar to that shown in FIG. 7, including a first exemplary embodiment of a handle for actuating the apparatus.

FIG. 23B is a cross-sectional detail of components of a rotary knob control on the handle of FIG. 23A with a housing of the handle removed to show internal components.

FIG. 25A is a perspective view of yet another apparatus, similar to that shown in FIG. 7, including a third exemplary embodiment of a handle for actuating the apparatus.

FIG. 25B is a cross-sectional detail of components of a rotary wheel control on the handle of FIG. 25A with a housing of the handle removed to show internal components.

DETAILED DESCRIPTION OF THE EXEMPLARY EMBODIMENTS

Figure 1:
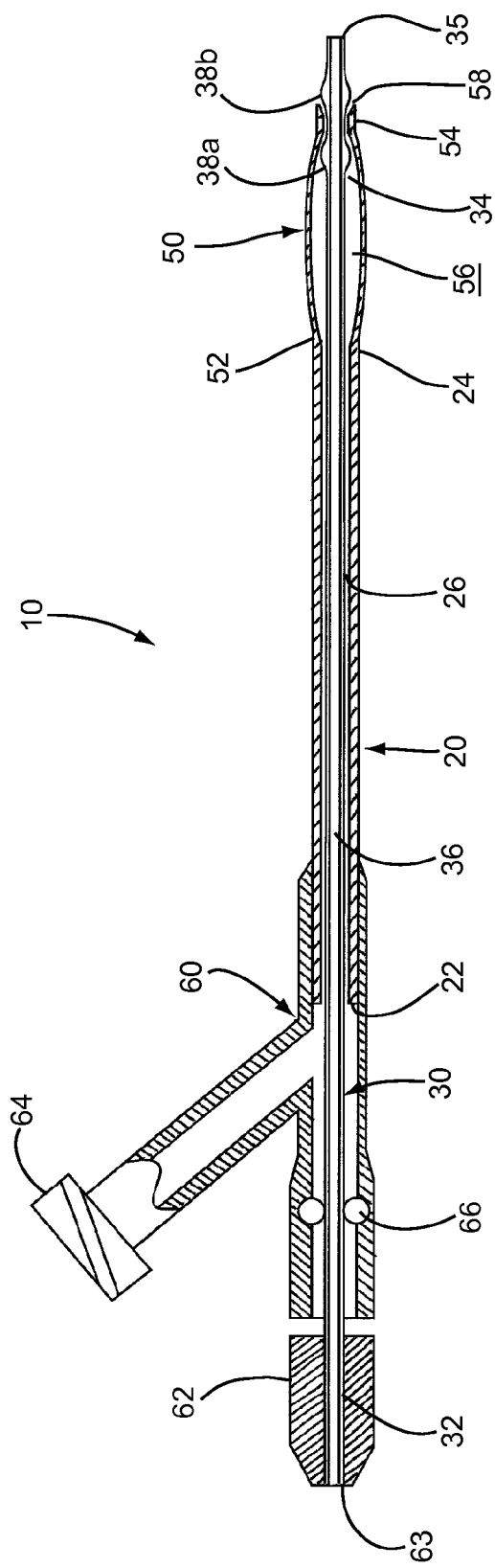
FIG. 1 is a side view of a first exemplary embodiment of an apparatus including a balloon for treating a body lumen, the apparatus operable in a first mode for minimizing a profile of the apparatus for introduction into the body lumen, a second mode for infusing fluid into the body lumen, and a third mode for removing material within the body lumen.

Turning to the drawings, FIGS. 1-5 show a first exemplary embodiment of an apparatus 10 for treating a body lumen, e.g., for infusing fluid into a body lumen and/or for removing thrombus, objects, and/or obstructive material from within a body lumen, such as a blood vessel, aorto-venous fistula, tubular graft, and the like (not shown). Generally, the apparatus 10 includes a catheter, sheath, or other tubular outer member 20, a core wire, shaft, or other elongate inner member 30, and an expandable balloon 50 carried by the inner and/or outer members 20, 30. The apparatus 10 may be operable in multiple modes, for example, to perform various treatments or other functions within a body lumen, e.g., to reduce or eliminate the need to exchange multiple devices during a procedure within a body lumen. For example, the apparatus 10 may be operable in a first mode for minimizing a profile of the apparatus 10, e.g., to facilitate introduction into a patient's body (FIG. 2), a second mode for infusing fluid into a body lumen (FIG. 3), and a third mode for removing material within a body lumen (FIGS. 4 and 5), as described further below.

As best seen in FIG. 1, the outer member 20 includes a proximal end 22, a distal end 24 sized for introduction into a body lumen, and a first lumen 26 extending therebetween. The outer member 20 may have a substantially uniform construction along its length, or alternatively, the construction may be varied. For example, a proximal portion of the outer member 20 may be substantially rigid or semi-rigid to facilitate advancement of the apparatus 10 from the proximal end 22 and/or a distal portion of the outer member 20 may be flexible, e.g., to facilitate bending and/or advancement through tortuous anatomy without substantial risk of kinking or buckling. In exemplary embodiments, the outer member 20 may be formed from materials such as metal, plastic, e.g., PEEK, Grilamed L25, and the like, or composite materials. The outer member 20 may have a length between about thirty and one hundred thirty centimeters (30-130 cm) and an outer diameter between about 1.2 to 2.0 millimeters, and the first lumen 26 may have a diameter between about 1.0 and 1.8 millimeters.

The inner member 30 also includes a proximal end 32, a distal end 34, and, optionally, may include a second lumen 36 extending between the proximal and distal ends 32, 34, which may be sized to slidably receive a guide wire, or other rail (not shown) therethrough, e.g., having a diameter between about 0.3 and 1.0 millimeter. The inner member 30 is sized to be slidably received within the first lumen 26 of the outer member 20, e.g., such that an annular space is defined between the outer and inner members 20, 30 for passing one or more fluids therethrough, as described further below. The inner member 30 may have a length relative to the outer member 20 such that the inner member proximal end 32 is received within or extends proximally beyond the outer member proximal end 22 and the inner member distal end 34 extends distally beyond the outer member distal end 24, e.g., through the balloon 50, as described further below.

The balloon 50 includes a proximal end 52 coupled to the outer member distal end 24, a distal end 54 defining an outlet 58, and an interior 56 communicating with the first lumen 26 and the outlet 58. The proximal end 52 of the balloon 50 may be attached or otherwise secured to the distal end 24 of the outer member 20 to provide a fluid-tight connection, e.g., by one or more of bonding with adhesive, interference fit, sonic welding, fusing, engagement with a surrounding sleeve or other connector (not shown), and the like.

The distal end 34 of the inner member 30 may extend through the distal end 54 of the balloon 50, e.g., such that the outlet 58 defines an annular passage between the distal end 54 of the balloon 50 and the distal end 34 of the inner member 30. The size of the outlet 58 may be substantially the same as the size of the first lumen 26, or alternatively, the outlet 58 may be larger or smaller than the first lumen 26, as desired, depending on the desired degree of friction or resistance to fluid flow through the outlet 58. For example, with the outlet 58 open to allow fluid flow, the resistance to fluid flowing through the outlet 58 may be substantially less than the resistance of the balloon 50 to expansion, such that the fluid preferentially flows through the outlet 58, rather than expanding the balloon 50, as described further below.

As shown in FIG. 1, the distal end 54 of the balloon 50 may be integrally formed with the main wall of the balloon 50 (defining the interior 56), and, optionally the proximal end 52 of the balloon 50. For example, the balloon 50 and its proximal and distal ends 52, 54 may be molded, blown, or otherwise formed from a single tubular section of material. Optionally, the main wall of the balloon 50 may be relatively thin compared to the distal end 54, e.g., such that the distal end 54 of the balloon 50 maintains its original size and/or shape as the balloon 50 is expanded.

For example, the distal end 54 of the balloon 50 may be sufficiently thick and/or rigid to provide a sealing ring on the distal end 54. Optionally, the distal end 54 of the balloon 50 may include one or more additional features, e.g., surrounding or otherwise defining the outlet 58 and/or reinforcing the distal end 54. For example, the distal end 54 may include a collar or sleeve (not shown, see, e.g., sleeve 155 shown in FIG. 7), within or around the distal end 54 e.g., attached or otherwise secured to the distal end 54, e.g., by bonding with adhesive, interference fit, sonic welding, fusing, and the like.

The balloon 50 may be formed from elastic material, e.g., to provide a compliant or semi-compliant balloon that may be expanded to a variety of sizes and/or shapes, e.g., based on the amount of fluid and/or pressure within the interior 54 of the balloon 50 and/or the relative position of the inner member 30, as described further below. Alternatively, the balloon 50 may be formed from substantially inelastic material, e.g., to provide a non-compliant balloon that expands to a predetermined size when inflated independent of pressure (once a minimum volume and/or pressure is introduced to achieve the predetermined size). Such a non-compliant balloon 50 may expand to the predetermined size even if inflated to relatively high pressures, e.g., until the balloon 50 bursts or otherwise ruptures, e.g., at pressures of ten atmospheres, twenty atmospheres, thirty atmospheres, and the like.

One or more sealing members 38 may be carried on the inner member distal end 34, e.g., such that the sealing member(s) 38 are movable relative to the balloon 50 as the inner member 30 is moved, e.g., for selectively opening and closing the outlet 58 of the balloon 50 to provide a valve, as described further below. The sealing member(s) 38 may be formed from flexible materials, e.g., which may enhance engagement with the balloon distal end 54, such as elastomeric materials, e.g., silicone, or other plastics, e.g., PEBAX.

As best seen in FIG. 1, a first sealing member 38a may be provided on the inner member 30 proximal to or otherwise adjacent a second sealing member 38b. The sealing member(s) 38 may be disposed adjacent a distal tip 35 of the inner member 30 or may extend beyond the distal tip 35. The distal tip 35 (or the sealing member extending beyond the distal tip 35) may be substantially atraumatic, e.g., rounded, softened, provided with a "J" tip, and the like (not shown), to facilitate advancement of the apparatus 10 within a patient's body without substantial risk of the distal tip 35 puncturing or otherwise damaging walls of body lumens through which the distal tip 35 passes.

The sealing member(s) 38 may have a size, e.g., outer diameter, that is larger than the distal end 54 of the balloon 50, e.g., larger than the inner diameter of the outlet 58. As shown in FIG. 1, the sealing members 38 are spaced apart sufficiently from one another such that the distal end 54 of the balloon 50 is free floating between the sealing members 38. When the inner member 30 is directed axially, one of the sealing members 38 may engage or otherwise contact the distal end 54 of the balloon 50. The sealing member(s) 38 may have tapered shapes to facilitate seating or other engagement by the sealing member(s) 38 with the distal end 54.

Figure 2:
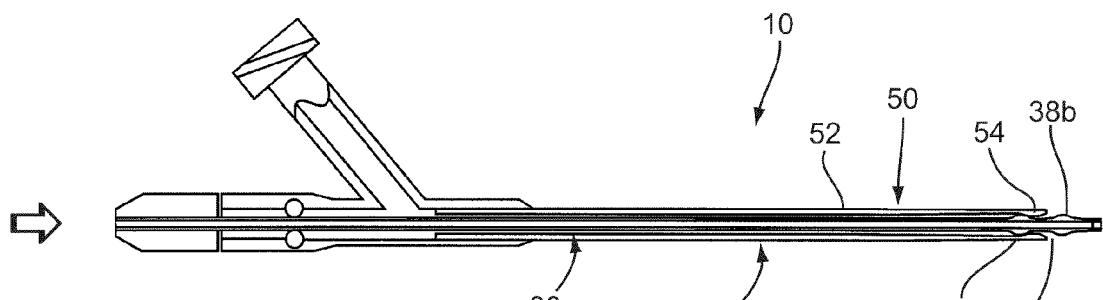
FIG. 2 is a side view of the apparatus of FIG. 1 in the first mode for minimizing a profile of the apparatus for introduction into a body lumen.

For example, with additional reference to FIG. 2, the inner member 30 may be directed distally to a first or distal position wherein the first sealing member 38a pushes or otherwise contacts the distal end 54, and the second sealing member 38b is spaced from the balloon outlet 58. As shown, the inner member 30 may be advanced distally to cause the first sealing member 38a to push the distal end 54. Because the outer diameter of the first sealing member 38a is larger than inner diameter of the distal end 54, the first sealing member 38a pushes the distal end 54 of the balloon 50 away from the proximal end 52 tie, thereby stretching the balloon 50. This configuration may minimize or otherwise reduce the profile of the balloon 50, e.g., to facilitate introduction into a patient's body. In this first position, the first sealing member 38a may substantially seal the outlet 58, although alternatively, the first sealing member 38a may include one or more axial grooves or other features that allow at least some fluid to pass through the outlet 58 even when the first sealing member 38a is seated or pushing against the distal end 54.

Figure 3:
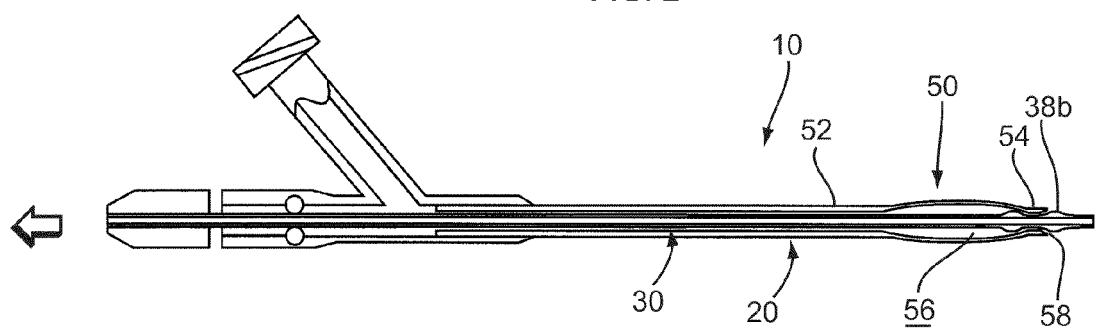
FIG. 3 is a side view of the apparatus of FIG. 1 in the second mode for infusing fluid into a body lumen.

Turning to FIG. 3, the inner member 30 may be directed axially to a second position, e.g., proximal to the first position, such that the distal end 54 of the balloon 50 is disposed between the sealing members 38a, 38b and the outlet 58 is substantially open. Thus, fluid introduced through the first lumen 26 of the outer member 20 may pass through the balloon interior 56 and exit through the outlet 58, e.g., between the balloon distal end 54 and inner member distal end 24 into the body lumen beyond the distal tip 35.

Figure 4:
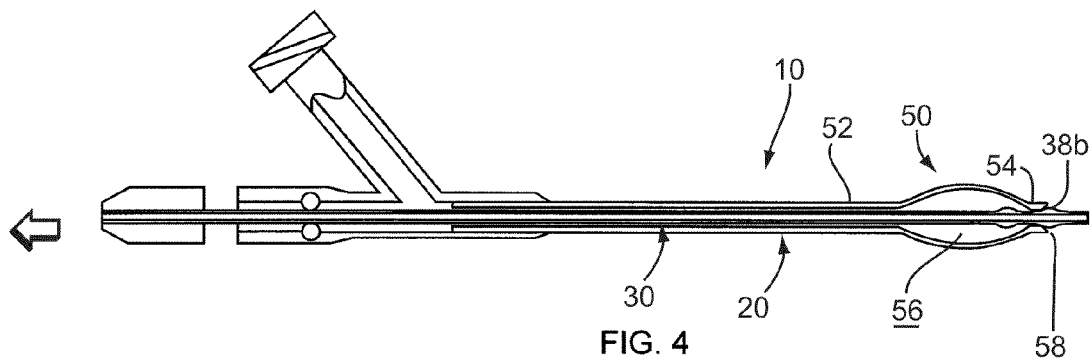
FIG. 4 is a side view of the apparatus of FIG. 1 in the third mode in which the balloon is expanded for removing material within a body lumen.
Figure 5:
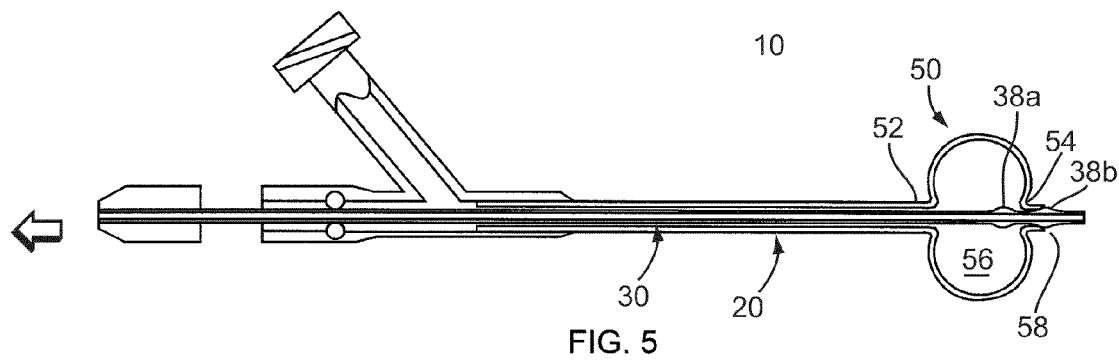
FIG. 5 is a side view of the apparatus of FIGS. 1 and 4 in the third mode, showing a size of the balloon being increased to facilitate removing material within a body lumen.

As shown in FIG. 4, the inner member 30 may also be directed proximally to a third position, e.g., proximal to the second position, in which the second sealing member 38b engages the distal end 54 of the balloon 50, thereby substantially sealing the outlet 58 from fluid flow therethrough. Thus, any fluid introduced through the first lumen 26 enters the balloon interior 56 and expands the balloon 50. Optionally, as shown in FIG. 5, once the balloon 50 is expanded, the inner member 30 may be directed further proximally, e.g., to an indefinite number of positions wherein the second sealing member 38b continues to seal the outlet 58, and the size and/or shape of the expanded balloon 50 may be changed. For example, as shown in FIG. 4, with the inner member 30 in the third position, the balloon 50 may be inflated to an elliptical or generally spherical shape, e.g., by delivering a predetermined volume of fluid into the interior 56 of the balloon 50. If the balloon 50 is compliant, one of a range of desired volumes may be delivered into the interior 56 to expand the balloon 50 to a desired diameter.

With further reference to FIG. 5, thereafter, as the inner member 30 is directed proximally further, the distal end 54 of the balloon 50 (captured between the sealing members 38) is also directed proximally, i.e., towards the proximal end 52 of the balloon 50, thereby compressing the balloon 50 axially and expanding the balloon 50 further.

Figure 6A:
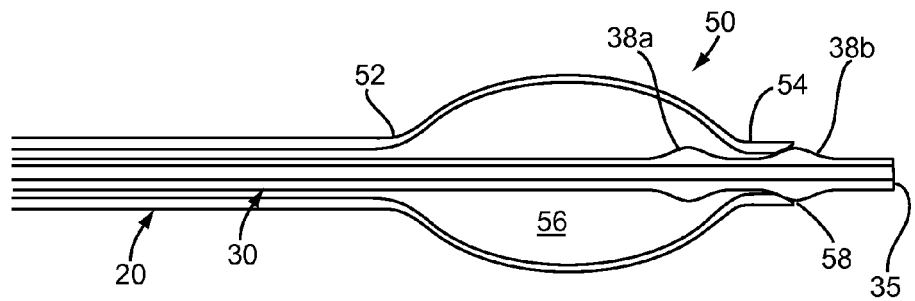
FIGS. 6A-6D are side view details of the apparatus of FIGS. 1-5, showing alternative configurations for the balloon.

As shown in FIG. 6A, the balloon 50 wall may have a substantially uniform wall thickness between the proximal and distal ends 52, 54. Thus, when the balloon is compressed, as shown in FIG. 5, the proximal and/or distal ends 52, 54 of the balloon 50 may at least partially evert into the interior 56 of the balloon 50. Thus, the wall of the balloon 50 may fold over onto the outside of the proximal and/or distal ends 52, 54 as the inner member 30 is directed proximally from the third position.

Figure 6B:
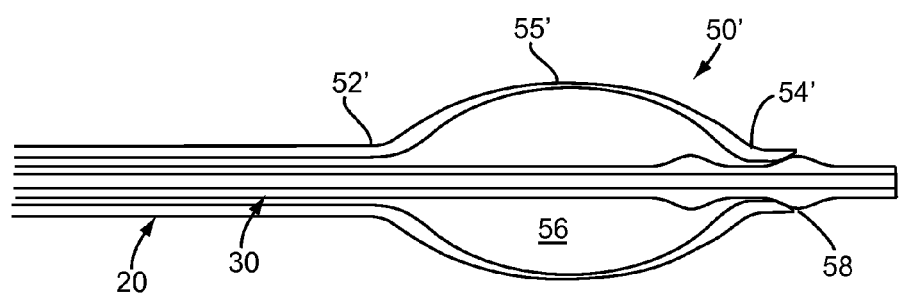

Alternatively, as shown in FIG. 6B, the thickness of the balloon 50' may be reduced along its length, e.g., thinning from the proximal and distal ends 52,' 54' towards a central region 55' of the balloon 50.' Thus, the regions of the balloon 50' immediately adjacent the proximal and distal ends 52,' 54' may be relatively rigid compared to the central region 55.' When the balloon 50' is compressed after expansion, the regions immediately adjacent the proximal and distal ends 52,' 54' may resist the balloon 50' everting and the thinner central region 55' may expand to a greater diameter compared to the balloon 50 of FIG. 6A.

Figure 6C:
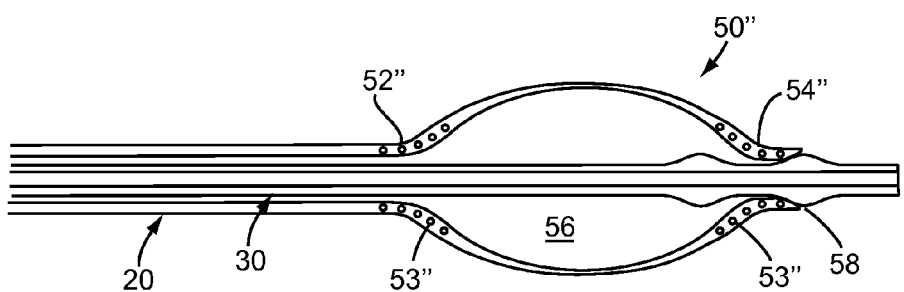
Figure 6D:
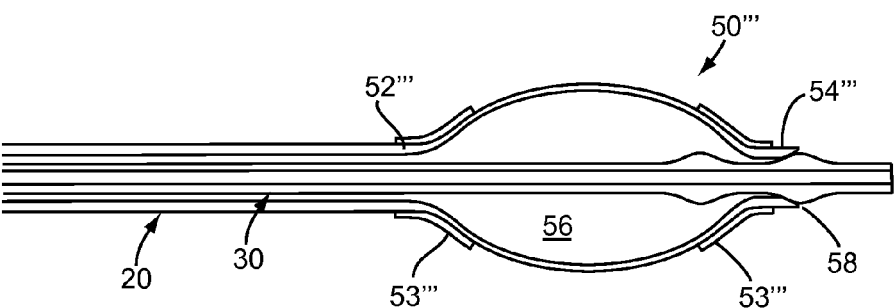

In further alternatives, shown in FIGS. 6C and 6D, the regions of the balloon 50," 50'" immediately adjacent the proximal and/or distal ends 52," 54" or 52,'" 54'"" may be reinforced further, e.g., including additional materials, to reinforce the base of the balloon 50," 50'" to reduce everting and/or otherwise preferentially control expansion of the balloon 50," 50.'" For example, in FIG. 6C, composite materials 53" have been embedded or otherwise provided in the balloon material adjacent the proximal and distal ends 52," 54," while in FIG. 6D, an additional layer of material 53'" has been added, which may be the same material or different material than the rest of the balloon 50.'" The layer may be attached to the balloon 50'" similar to the materials and methods described elsewhere herein for attaching the balloon 50'" to the outer member 20.

Returning to FIG. 1, a handle or hub 60 may be coupled to or otherwise provided on the proximal end 22 of the outer member 20, e.g., for manipulating the outer member 20 and/or the entire apparatus 10. The handle 60 may have an ergonomic shape, e.g., to facilitate holding and/or manipulating the handle 60, and including one or more controls or actuators for actuating the components of the apparatus 10. For example, as shown, a pull handle 62 may be provided adjacent the main handle 60 that is coupled to the inner member 30. Thus, to move the inner member 30 to the various positions described above, the pull handle 62 may be pushed or pulled, e.g., pushed distally to direct the inner member 30 to the first position shown in FIG. 2, and pulled proximally to direct the inner member 30 to the second and third (or further proximal) positions, shown in FIGS. 3-5. Alternatively, similar to the embodiments shown in FIGS. 11 and 14, a slider actuator (not shown) may be provided on the handle 60 that is coupled to the inner member 30 for directing the inner member 30 axially relative to the handle 60 and outer member 20. In a further alternative, a wheel or other actuator may be provided for directing the inner member 30 axially relative to the outer member 20.

The pull handle 62 and/or inner member 30 may be biased to one of the positions shown in FIGS. 2-5, e.g., by one or more springs or other biasing mechanisms (not shown) within the handle 60. For example, the inner member 30 may be biased to the second (infusion) position, but may be directed to the other positions by overcoming the bias. Alternatively, the handle 60 may include one or more features, e.g., pockets, notches, and the like (not shown), providing tactile feedback and/or for releasably securing the inner member 30 in one of the positions. In addition or alternatively, the handle 60 may include one or more visual markers (not shown), e.g., to inform the user when the various positions are achieved. In a further alternative, the first sealing member 38a may be eliminated and the first position eliminated, e.g., if there is less concern with profile of the apparatus 10 during introduction and/or to simplify operation of the apparatus 10.

With continued reference to FIG. 1, the handle 60 may also include one or more ports for coupling one or more fluid sources to the apparatus 10, such as a source of inflation media, a source of vacuum, and/or a source of diagnostic and/or therapeutic agents (not shown). For example, as shown, a side port 64 may communicate with the first lumen 26. The side port 64 may include one or more connectors (not shown) to facilitate coupling one or more sources of fluid to the side port 64, e.g., a Luer lock connector, and/or one or more seals, e.g., a hemostatic seal, to prevent fluid from leaking from the side port 64.

A syringe or other source of fluid (not shown) may be coupled to the side port 64 to allow delivery of the fluid through the first lumen 26 into the interior 56 of the balloon 50 and/or through the outlet 58, depending upon the position of the inner member. For example, if the inner member 30 is in the second (infusion) position, contrast material, e.g., radiopaque, echogenic, or other fluid that facilitates observation using fluoroscopy, ultrasound, or other external imaging, may be delivered through the first lumen 26 and outlet 58 into a body lumen. Such material may facilitate monitoring the apparatus 10 during advancement through a patient's body into a target body lumen and/or to identify the status of treatment of a body lumen, as described further below. With the inner member 30 in the third position, the same fluid may be delivered through the first lumen 26 to expand the balloon 50, or the source of contrast material may be replaced with a source of a different fluid, e.g., a syringe of saline, to facilitate expansion and/or collapse of the balloon 50.

Alternatively, multiple ports may be provided that communicate with the first lumen 26, e.g., such that various fluids may be delivered selectively through the first lumen 26 depending upon the desired function. For example, a source of contrast and a source of saline could be coupled to different ports such that each fluid may be delivered independently depending upon the position of the inner member 30 without having to change out the sources. Alternatively, a source of one or more therapeutic agents may be coupled to the side port 64 (or to a separate port), e.g., when desired, to deliver the agent(s) into the target body lumen.

Optionally, the handle 60 may include one or more seals, bushings, and the like to facilitate relative motion of the outer and inner members 20, 30 and/or to seal the first lumen 26. For example, as shown in FIG. 1, an o-ring 66 may be provided between the outer and inner members 20, 30, which may guide the inner member 30 as it moves axially relative to the outer member 30 and handle 60. The o-ring 66 may also be located proximal to the side port 64, thereby providing a substantially fluid-tight seal between the outer and inner members 20, 30 to prevent leakage of fluid introduced into the side port 64 from the handle 60.

As shown, the pull handle 62 includes a port 63 for receiving a guidewire or other rail (not shown) therethrough. For example, a guidewire may be introduced into the second lumen 36, e.g., from the port 63 or by backloading into the inner member distal end 34. The port 63 may include one or more seals, e.g., a hemostatic seal (not shown), to accommodate passage of a guidewire through without risk of substantial risk of leakage of blood or other body fluids from the second lumen 36.

Optionally, the outer member 20 may include one or more additional lumens (not shown) extending between the proximal and distal ends 22, 24, e.g., a guidewire lumen for receiving a guidewire or other rail (not shown), e.g., if the inner member 30 does not include the second lumen 36, an inflation lumen for delivering inflation media to another balloon (not shown) on the distal end 24, and the like.

In addition or alternatively, if desired, the apparatus 10 may include one or more markers to facilitate positioning and/or advancement of the apparatus 10 during use. For example, one or more radiopaque markers may be placed on the outer member distal end 24, on the inner member 30 within or adjacent the balloon 50 or distal tip 35, on the balloon 50, e.g., on the proximal and/or distal ends 52, 54, and/or on the sealing member(s) 38. Alternatively, one or more components of the apparatus 10 may be formed from radiopaque or other materials that may facilitate imaging the apparatus 10 during use. For example, radiopaque markers and/or materials may facilitate positioning or otherwise imaging the apparatus 10 using fluoroscopy or other x-ray imaging, e.g., when positioning the balloon 50 (either before or after expansion) and/or when infusing fluid via the outlet 48. Alternatively, echogenic markers and/or materials may be provided to facilitate imaging using ultrasound or similar imaging techniques.

With continued reference to FIGS. 2-5, an exemplary method will now be described for treating a body lumen (not shown), e.g., using an apparatus 10, which may be any of the embodiments described herein, and not necessarily limited to the embodiment shown and described below with reference to FIG. 1. The target body lumen may be a blood vessel, e.g., a vein or artery, a graft, e.g., an aorto-venous fistula, tubular xenograft, or synthetic tubular graft, and the like. For example, the body lumen may be a passage communicating between an adjacent artery and vein (not shown), e.g., in an arm or other region of a dialysis patient. Alternatively, the body lumen may be a blood vessel within a patient's vasculature, e.g., a peripheral vessel in a patient's leg, a cerebral vessel, and the like. In a further alternative, the material may be a stone within a patient's urinary tract or other foreign object to be removed from the patient's body.

Optionally, the body lumen may be accessed using one or more additional instruments (not shown), which may be part of a system or kit including the apparatus 10. For example, an introducer sheath, guide catheter, or other tubular member (not shown) may be introduced adjacent the target site where the material is to be removed, or may be introduced elsewhere in the patient's body to provide access to the patient's vasculature or other passages communicating with the body lumen. If the body lumen is located in a peripheral vessel of the patient, a percutaneous puncture or cut-down may be created using a needle or other instrument (not shown) at a peripheral location, such as a femoral artery, carotid artery, or other entry site (also not shown), and an introducer sheath may be placed through the puncture at the peripheral location to provide access. The apparatus 10 may be advanced through the patient's vasculature from the entry site, e.g., alone or with the aid of a guide catheter, guidewire, and the like (not shown).

For example, to facilitate directing the apparatus 10 from an entry site to the target body lumen, a guide catheter, microcatheter, or other tubular body may be placed from the entry site to the body lumen using conventional methods. In addition or alternatively, a guidewire (not shown) may be placed from the entry site to the body lumen if desired, e.g., if the inner member 30 includes the second lumen 36. The tubular body may also be used for aspiration, e.g., coupled to a source of vacuum for capturing material removed by the apparatus 10.

Initially, with reference to FIG. 2, the apparatus 10 may be advanced into the body lumen with the inner member 30 in the second or distal position, e.g., such that the balloon 50 is stretched to reduce its profile. Optionally, if the first sealing member 38a does not seal the outlet 58, one or more fluids may be delivered into the body lumen, e.g., to facilitate imaging and/or positioning the apparatus 10. Alternatively, the inner member 30 may be directed to the first position, shown in FIG. 3, and fluid delivered to facilitate imaging.

For example, radiopaque contrast or other fluid may be delivered into the body lumen via the annular passage defined by the first lumen 26 between the outer and inner members 20, 30 to facilitate locating and/or measuring the size of the material 92 using fluoroscopy. Markers (not shown) on the apparatus 10 may facilitate positioning the balloon 50 relative to material intended to be removed before the balloon 50 is expanded, e.g., to facilitate verifying that the balloon 50 is positioned distal to or otherwise beyond the material. If desired, the inner member 30 may be directed back and forth between the first and second positions, e.g., to allow infusion of contrast and to reduce the profile of the apparatus 10 to facilitate further advancement, e.g., until the balloon 50 is located beyond obstructive material targeted for removal.

Optionally, the apparatus 10 may be introduced through a guide catheter or other tubular member (not shown), that includes a lumen communicating with a source of vacuum. With the balloon 50 disposed beyond the guide catheter but not yet expanded, the source of vacuum may be activated to aspirate material within the body lumen during the subsequent treatment.

Turning to FIG. 4, the inner member 30 may be directed to the third position, thereby sealing the outlet 58, and the balloon 50 may be inflated within the body lumen, e.g., such that the balloon 50 extends substantially entirely across the body lumen. The entire apparatus 10 may then be retracted to pull the occlusive material from the body lumen, e.g., to be aspirated into guide catheter, or otherwise removed from the body lumen. As shown in FIG. 5, if desired, the inner member 30 may be pulled to further expand the balloon 50, e.g., to substantially engage the wall of the body lumen. The additional pressure from the balloon 50 may facilitate separating adherent material from the wall of the body lumen and allow its removal.

Once material is removed, the inner member 30 may be directed back towards the second position, and fluid introduced to observe the amount of material removed and/or remaining within the body lumen. If additional material is to be removed, the inner member back be directed to the first position, e.g., if desired to advance the apparatus 10 through additional material to be removed. Once the balloon 50 is located beyond the material, the process may be repeated as often as desired.

If desired, the obstructive material may be treated, e.g., at least partially dissolved, macerated, and the like before, during, or after withdrawal. For example, a therapeutic agent may be delivered into the body lumen via the first lumen 26 of the outer member 20, e.g., to at least partially dissolve or separate thrombus or other relatively soft material before being removed by the balloon 50 and/or otherwise to treat the wall of the body lumen.

Because a single lumen, i.e., the first lumen 26, is used for both inflation of the balloon 50 and delivering fluid into the body lumen, the profile of the outer member 20 and therefore of the overall apparatus 10 may be smaller than devices that include separate inflation and infusion lumens. Further, although the second lumen 36 of the inner member 30 could be used for infusion of fluids, this would generally require removing the guidewire over which the apparatus 10 is introduced since the guidewire may substantially fill the second lumen 36. Because the first lumen 26 may be used for infusion, the guidewire may remain within the second lumen 36 throughout the procedure, thereby potentially reducing the number of guidewire or other device exchanges. Further, the apparatus 10 may remain over the guidewire, which may facilitate advancing the apparatus 10 to other target body lumens intended for treatment.

In various alternatives, the valve created by the sealing member(s) 38 and the outlet 58 of the balloon 50 may be provided at other locations on the apparatus 10, if desired. For example, the configuration may be reversed such that the outlet 58 and sealing members 38 may be located proximal to the balloon 50. For example, a sealing member (not shown) may be provided on the distal end 24 of the outer member 20, and the proximal end 52 of the balloon 50 may float adjacent the sealing member(s), with the distal end 54 of the balloon 50 is secured to the distal end 34 of the inner member 30 (also not shown). Thus, movement of the inner member 30 relative to the outer member 20 may cause the balloon proximal end to selectively engage or disengage the sealing member(s), allowing infusion from the first lumen 24 when the balloon proximal end is not engaged with the sealing member(s) and allowing balloon inflation when the balloon proximal end engages the sealing member(s).

In another alternative, a balloon (not shown) may be provided on the distal end 24 of the outer member 20 proximal to the balloon 50 and/or on the distal end 34 of the inner member 30 distal to the balloon 50, if desired, similar to other embodiments described herein. Such a balloon may be a non-compliant, high pressure balloon, e.g., for dilating the body lumen, or an elastic, compliant balloon for substantially sealing the body lumen to isolate one or more regions of the body lumen before infusion of fluid therein.

Figure 7:
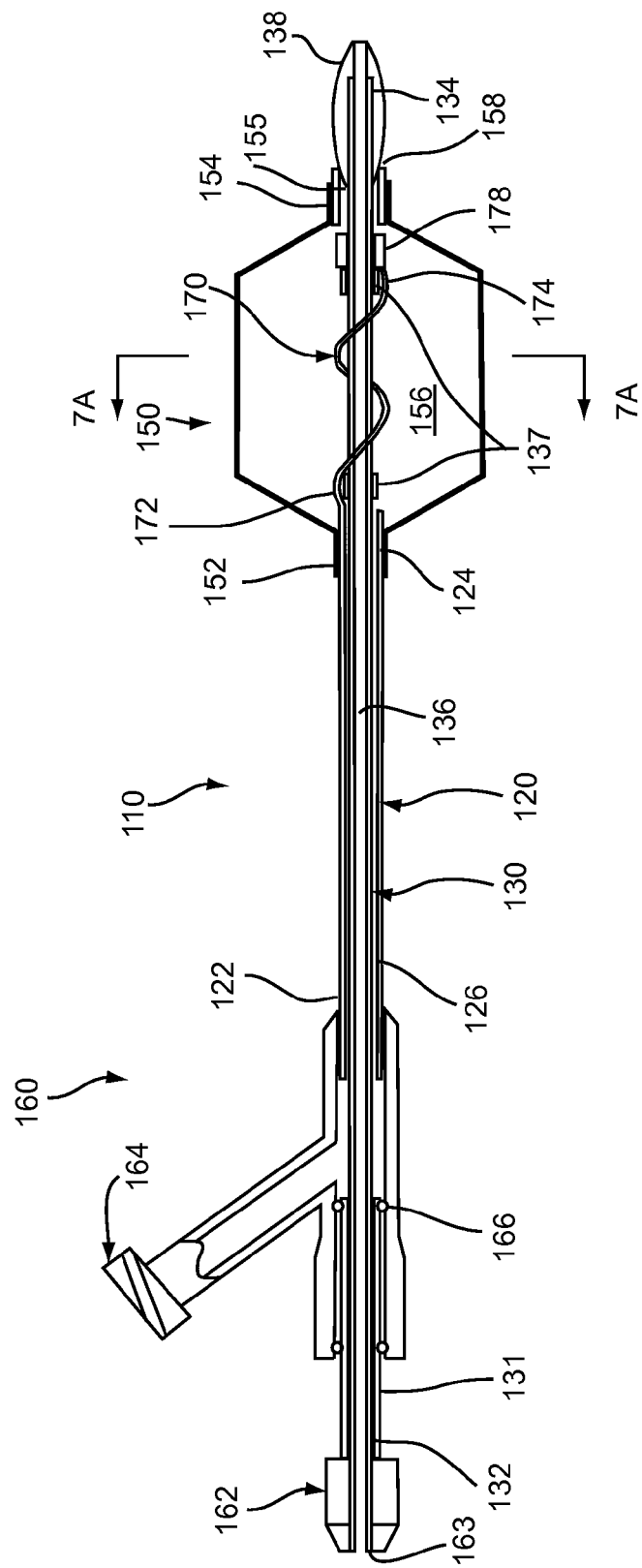
FIG. 7 is a side view of a second exemplary embodiment of an apparatus including a balloon for treating a body lumen, the apparatus operable in a first mode for infusing fluid into the body lumen, a second mode for dilating an obstruction within the body lumen, and a third mode for removing material within the body lumen.

Turning to FIG. 7, another embodiment of an apparatus 110 is shown for treating a body lumen that generally includes an outer tubular member 120, an inner member 130, and an expandable balloon 150 carried by the inner and/or outer members 120, 130, similar to the previous embodiments. The apparatus 110 may be operable in a first mode for infusing fluid into a body lumen, a second mode for dilating an obstruction within a body lumen, and/or a third mode for removing obstructive material within a body lumen, as described further below.

As shown, the outer member 120 includes a proximal end 122, a distal end 124 sized for introduction into a body lumen, and a first lumen 126 extending therebetween, which may be constructed similar to the previous embodiments. The inner member 130 also includes a proximal end 132, a distal end 134, and, optionally, a second lumen 136 extending between the proximal and distal ends 132, 134, e.g., sized to slidably receive a guide wire, or other rail (not shown) therethrough. The inner member 130 is sized to be slidably received within the first lumen 126 of the outer member 120, e.g., such that an annular space is defined between the outer and inner members 120, 130 for passing one or more fluids therethrough, also similar to the previous embodiments.

The balloon 150 includes a proximal end 152 coupled to the outer member distal end 124, a distal end 154 defining an outlet 158, and an interior 156 communicating with the first lumen 126 and the outlet 158. The distal end 134 of the inner member 130 may extend through the distal end 154 of the balloon 150, e.g., such that the outlet 158 defines an annular passage between the distal end 154 of the balloon 150 and the distal end 134 of the inner member 130. As shown, the distal end 154 of the balloon 150 includes a collar or sleeve 155 attached or otherwise secured to the distal end 154, e.g., by bonding with adhesive, interference fit, sonic welding, fusing, and the like. Optionally, the collar 155 may extend proximally into the interior 156 of the balloon 150 (not shown) and the interior section of the collar 155 may include one or more side ports or other openings (also not shown), e.g., to facilitate fluid passing from the balloon interior 156 through the outlet 158.

The balloon 150 may be formed from substantially inelastic material, e.g., to provide a non-compliant balloon that expands to a predetermined size when inflated independent of pressure (once a minimum volume is introduced to achieve the predetermined size). Such a non-compliant balloon 150 may expand to the predetermined size even if inflated to relatively high pressures, e.g., until the balloon 150 bursts or otherwise ruptures, e.g., at pressures of ten atmospheres, twenty atmospheres, thirty atmospheres, and the like. Alternatively, the balloon 150 may be formed from elastic material, similar to other embodiments described elsewhere herein.

One or more sealing members 138 may be carried on the inner member distal end 134, e.g., such that the sealing member(s) 138 are movable relative to the balloon 150 as the inner member 130 is moved, e.g., to provide a valve for selectively opening and closing the outlet 158 of the balloon 150. As shown, a first sealing member 138 is provided on the inner member 130 distal to the balloon distal end 154 and collar 155. The sealing member 138 may have a size, e.g., outer diameter, that is larger than the collar 155 and distal end 154 of the balloon 150 such that the sealing member 138 may substantially engage the collar 155 and/or distal end 154 of the balloon 150 to substantially seal the outlet 158.

In the exemplary embodiment shown, the sealing member 138 may include a tapered shape, e.g., on one or both of its proximal and distal ends. For example, a tapered shape on the proximal end of the sealing member 138 may automatically guide the sealing member 138 into being seated in the outlet 158 of the balloon 150, e.g., to enhance a fluid-tight seal therebetween. A tapered shape on the distal end of the sealing member 138 may provide a rounded or otherwise substantially atraumatic tip for the apparatus 110. Alternatively, a substantially atraumatic distal tip (not shown) may be provided on the inner member 130 beyond the first sealing member 138, similar to the previous embodiments.

With continued reference to FIG. 7, a handle or hub 160 may be coupled to or otherwise provided on the proximal end 122 of the outer member 120, e.g., for manipulating the outer member 120 and/or the entire apparatus 110, generally similar to the previous embodiments. The handle 160 may include a pull handle 162 or other actuator coupled to the inner member 130 for moving the inner member 130 to the various positions described below. The handle 160 may also include one or more ports, such as port 163 and side port 164 for coupling one or more fluid sources to the apparatus 110, e.g., a syringe or other source of fluid for delivering fluid through the first lumen 126 into the interior 156 of the balloon 150 and/or through the outlet 158, depending upon the position of the inner member 130.

Optionally, the handle 160 may include one or more seals, bushings, and the like, such as o-ring 166, between the outer and inner members 120, 130, which may guide the inner member 130 as it moves axially relative to the outer member 130 and handle 160. In this embodiment, the inner member 130 includes a section of hypotube or other substantially rigid tubing 131 attached or otherwise coupled to the proximal end 132 of the inner member 130. The tubing 131 may provide axial support for the inner member 130, e.g., to prevent buckling or kinking when the inner member 130 is directed axially. The tubing 131 may also allow the inner member 130 to move axially more easily, e.g., if the tubing 131 has a substantially smooth or lubricated outer surface that slides easily through the o-ring 166 while maintaining a fluid-tight seal therebetween.

In addition or alternatively, if desired, the apparatus 110 may include one or more markers to facilitate positioning and/or advancement of the apparatus 110 during use. For example, as shown in FIG. 7, radiopaque marker bands 137 may be attached around the distal end 134 of the inner member 130, e.g., within the balloon interior 56. As shown, a marker 137 is attached adjacent both the proximal end 152 and the distal end 154 of the balloon 150, which may facilitate monitoring the location of the balloon 150 before dilating an obstruction within a body lumen. In addition or alternatively, a core wire of the helical member 170 may be formed from radiopaque material, and/or radiopaque filler material, BAS04, may be dispersed into plastic material used to form the helical member 170, if desired.

Unlike the previous embodiments, the apparatus 110 includes a helical member 170 coupled between the outer and inner members 120, 130 within the balloon interior 156. The helical member 170 may be movable from a relatively low profile, such as that shown in FIG. 7, to an expanded helical shape, as described further below. As shown, the helical member 170 is a wire, tube, or other filament including a first end 172 coupled to the distal end 124 of the outer member 120 and a second end 174 coupled to the distal end 134 of the inner member 130. For example, the helical member 170 may be from a core wire having a tube or sleeve formed or attached around the wire (not shown). Between the first and second ends 172, 174, the helical member 170 may wrap helically around the inner member 130 one or more times. As shown, the helical member 170 extends around the inner member 130 about one and a half turns, although it will be appreciated that the helical member 170 may include more or fewer turns.

As shown, the first end 172 of the helical member 170 may be attached or otherwise secured directly to the distal end 124 of the outer member 120, e.g., by one or more of bonding with adhesive, sonic welding, soldering, interference fit (e.g., by wrapping the first end 172 one or more times around the distal end 124), inserting the first end 172 into an annular groove, hole, or pocket (not shown) in the distal end 124, fusing, and the like. The second end 174 of the helical member 170 may be similarly attached or otherwise secured to a sleeve 178 fixed to the distal end 134 of the inner member 130 or directly to the distal end 134.

The sleeve 178 may be a relatively short tube attached to the inner member distal end 134 adjacent the balloon distal end 154, e.g., by bonding with adhesive, sonic welding, interference fit, fusing, and the like. The sleeve 178 may have an outer diameter larger than the inner diameter of the collar 155 and/or distal end 154 of the balloon 150, thereby providing a stop that limits movement of the collar 155 and distal end 154 relative to the inner member 130. When the sleeve 178 contacts the collar 155 and/or distal end 154, the sleeve 178 may not substantially obstruct the annular passage communicating with the outlet 158, e.g., such that fluid may still flow through the outlet 158 when introduced into the balloon interior 156. Alternatively, the sleeve 178 may be shaped to substantially seal the outlet 158 when the sleeve 178 engages the collar 155 and/or distal end 154 of the balloon 150, similar to the other sealing members described elsewhere herein. Optionally, during manufacturing or assembly, the collar 155 may be positioned between the sealing member 138 and the sleeve 178 when the collar and sleeve 178 are attached to the inner member distal end 134, i.e., before attaching the collar 155 to the balloon distal end 154. The balloon distal end 154 may then be attached over the collar 155 when the balloon 154 is attached to the outer member distal end 124. If desired, the balloon distal end 154 may be attached to the collar 155 such that a proximal section of the collar 155 is disposed within the interior 156 of the balloon 150. If so, the proximal section of the collar 155 may include one or more openings (not shown) to facilitate fluid passing from the balloon interior 156 through the collar 155 and out the outlet 158, i.e., when the outlet 158 is not sealed by the sealing member 138, as described further below.

The inner member 130 may be movable axially relative to the outer member 120, e.g., between a first or distal position, a second or intermediate position (shown in FIG. 7), and/or a third or proximal position (not shown), thereby allowing the apparatus 110 to provide different functions for treating a body lumen. For example, in the first position, the inner member 130 may direct the sealing member 138 distally such that the sealing member 138 is spaced apart from the balloon outlet 158. Thus, fluid introduced through the first lumen 126 of the outer member 120 may pass through the balloon interior 156 and out the outlet 158, e.g., into the body lumen beyond the distal tip 35, similar to the previous embodiments.

If desired, the inner member 130 may be directed proximally to a second position, such as that shown in FIG. 7, in which the sealing member 138 engages the collar 155 and/or distal end 154 of the balloon 150, thereby substantially sealing the outlet 158 from fluid flow therethrough. Thus, any fluid introduced through the first lumen 126 enters the balloon interior 156 and may expand the balloon 150. In this mode, the balloon 150 may be expanded to an elongate substantially cylindrical shape, e.g., having a substantially uniform diameter main portion between tapered end portions. In the expanded condition, the main portion of the balloon 150 may have a length between about twenty and eighty millimeters (20-80 mm) and a diameter between about three and twelve millimeters (3-12 mm). The balloon 150 may be used to dilate or otherwise apply substantial pressure to a wall of a body lumen, e.g., for dilating a stenosis, lesion, or other obstruction, similar to the method shown in FIGS. 9E-9G and described further below.

In addition or alternatively, after inflating the balloon 150 to dilate the body lumen, a source of vacuum may be coupled to the side port 164 and the balloon 150 collapsed to a contracted condition around the helical member 170. Alternatively, if the balloon 150 has not been previously inflated, it may not be necessary to collapse the balloon 150 using vacuum since the balloon 150 may already be sufficiently collapsed or otherwise remain in the contracted condition.

The inner member 130 may then be directed proximally to the third position, thereby directing the ends of the helical member 170 towards one another. This causes the helical member 170 to expand radially outwardly as it is compressed axially, thereby causing the balloon 150 also to compress axially and expand radially into an expanded helical shape around the helical member 170, e.g., as shown in FIG. 7A. Optionally, the inner member 130 and/or handle 150 may include one or more stops (not shown) that limit proximal movement of the inner member 130 when compressing and expanding the balloon 150 and helical member 170. For example, the stop(s) may allow the inner member 130 to be pulled until the balloon length is reduced to between about six and thirty millimeters (6-30 mm), thereby preventing overcompression of the balloon 150 and/or helical member 170.

In one embodiment, the helical member 170 may have sufficient rigidity that the helical member 170 may simply buckle elastically from the low profile towards the helical shape as it is compressed axially. Thus, the helical member 170 may expand without substantial plastic deformation such that the helical member 170 may be returned to its original low profile shape (and expanded and collapsed repeatedly, if desired). Alternatively, the helical member 170 may be biased to a predetermined expanded helical shape but may be constrained in the low profile, e.g., by providing axial tension on the ends 172, 174 of the helical member 170 when the inner member 130 is in the first or second positions. As the inner member 130 is directed towards the third position, the tension may be released, whereupon the helical member 170 may resiliently expand towards the expanded helical shape.

In another alternative, the helical member may be integrally formed or otherwise coupled directly to the balloon 150, e.g., attached to, embedded within, or otherwise secured to the balloon wall (not shown) between the proximal and distal ends 152, 154. For example, as shown in FIGS. 7B and 7D, one or more helically shaped wires or fibers 157' (e.g., one shown in FIG. 7B, two shown in FIG. 7D) may be molded, embedded, or integrally formed in the wall of the balloon 150.' As the balloon 150' is compressed axially when the inner member 130 is moved towards the third position, the fiber(s) 157' may automatically bias the balloon 150' towards the expanded helical shape. Alternatively, as shown in FIG. 7C, a fiber 157" may be molded, embedded, or integrally formed in the wall of the balloon 150" that includes a core wire or member 159," e.g., a radiopaque material, a biased core wire, and the like. In further alternatives, FIGS. 7E-7H show alternate shapes and/or configurations for a fiber $157_e$ to $157_h$ or other stiffening features that may be molded, embedded, or otherwise integrally formed in the wall of the balloon $150_e$ to $150_h$ and extend helically between proximal and distal ends of the balloon $150_e$ to $150_h$. The fiber(s) and/or stiffening features may include one or more turns between the proximal and distal ends of the balloon 150', 150", or $150_e$ to $150_h$, e.g., one and a half, two, three, four, or more turns. In addition, any of the fibers and/or stiffening features included on a balloon may provide cutting edges or elements, e.g., that may be at least partially embedded into a wall of a body lumen when the balloon 150', 150", or $150_e$ to $150_h$ is inflated to dilate an obstruction in a body lumen.

Returning to FIG. 7, with the balloon 150 in the expanded helical shape, the entire apparatus 110 may be directed along a body lumen, e.g., to remove obstructive material including scraping, scrubbing, or otherwise separating adherent material from a wall of the body lumen, if desired, similar to the method shown in FIGS. 9A-9D and described further below. Thus, in this embodiment, a single balloon 150 may be used for both dilation, e.g., using relatively high pressures, and for scraping, scrubbing, or otherwise removing obstructive material within a body lumen.

Turning to FIGS. 23A and 23B, an apparatus 110' is shown that is generally similar to the apparatus 110 of FIG. 7, i.e., including a balloon 150' and a helical member 170,' except that the apparatus 110' includes an alternative embodiment of a handle 760 on the proximal end 122' of the outer member 120.' Generally, the handle 760 includes an outer housing 761 (shown in FIG. 23A), an inner carriage 765 (shown in FIG. 23B) slidable axially within the housing 761, a rotary knob 762 carried by the housing 761 and coupled to the carriage 765, and a hub 763 extending from the housing 761.

The housing 761 may include one or more pieces, e.g., one or more sets of mating halves or clamshells (not shown) that may be connected together, e.g., along a longitudinal seam (also not shown) to provide the housing 761, e.g., secured together by mating connectors, bonding with adhesive, sonic welding, fusing, and the like. The housing 761 may include a slot, track or other features (not shown) that allow the carriage 765 to slide axially within the housing 761 without substantial lateral movement. The housing 761 and/or carriage 765 may include one or more cooperating features, e.g., stops (not shown) within the housing 761 that limit axial movement of the carriage 765 relative to the housing 761, for example, to limit movement of the inner member 130' between the first position (for infusion from the outlet 158') and the third position (where the balloon 150' is directed to an expanded helical shape, not shown).

The housing 761 may include a side port 764, e.g., including a Luer lock or other connector, for connecting a source of fluid to the apparatus 110.' The side port 764 may communicate with a lumen extending through the outer member 120' for delivering fluid into the interior of the balloon 150,' similar to the previous embodiments.

The knob 762 may include an outer portion 762a surrounding or otherwise extending radially from the housing 761, e.g., including ridges or other features to facilitate rotation or other manipulation of the knob 762 during use, and an inner stem 762b that extends axially along a first passage 765a within the carriage 765. The inner stem 762b and the carriage 765 may include cooperating features, e.g., helical threads 762c, that translate rotation of the knob 762 into axial movement of the carriage 765. Thus, the knob 762 may be substantially fixed axially relative to the housing 761 and freely rotatable about a longitudinal axis of the apparatus 110.'

The proximal end 132' of the inner member 130' may pass freely through the inner stem 762b and be fixed relative to the carriage 765. For example, the inner member proximal end 132' may be secured to the carriage 765 by fixing the proximal end 132' in a second passage 765b adjacent to and/or communicating with the first passage 765a, e.g., bonding with adhesive, sonic welding, fusing, interference fit, mating connectors (not shown), and the like. Thus, axial movement of the inner member 130' may be coupled to movement of the carriage 765.

The hub 763 may include a hypotube or other tubular member 763a and a Luer lock or other connector 763b secured to one another and/or to the outer housing 761. For example, a proximal end of the tubular member 763a and/or the connector 763b may be attached to a proximal end of the housing 761, e.g., by bonding with adhesive, sonic welding, fusing, interference fit, mating connectors (not shown), and the like.

The tubular member 763a may be slidably received in the second passage 765b such that the tubular member 763a and connector 763b remain substantially stationary relative to the housing 761 as the carriage 765 is directed axially. One or more seals, e.g., o-ring 766, may be provided within or around the second passage 765b that allow the tubular member 763a to slide therethrough while providing a fluid-tight seal that prevents fluid from leaking through the passages 765a, 765b and out of the housing 761.

During use, the knob 762 may be rotated in a first direction, thereby translating the inner member 130' distally to the first position to open the outlet 158.' Thus, fluid delivered through the outer member 120' may pass through the balloon 150' and exit the outlet 158,' as described above. The knob 762 may be rotated in a second opposite direction, thereby translating the inner member 130' proximally to the second position, e.g., until the sealing member 138' seals the outlet 158' to allow balloon expansion, and/or further to the third position, e.g., to expand the balloon 150' to the expanded helical shape, also as described above. Optionally, the knob 762 and/or housing 761 may include visual, audible, or other indicators (not shown) that identify the direction to rotate the knob 762 to achieve the desired position(s) and/or that indicate when a particular position is achieved, e.g., by aligning an arrow (not shown) on the knob 762 with respective indicators (also not shown) that identify the first, second, and/or third positions. Otherwise, the apparatus 110' may operate similar to the previous embodiments.

Figure 24A:
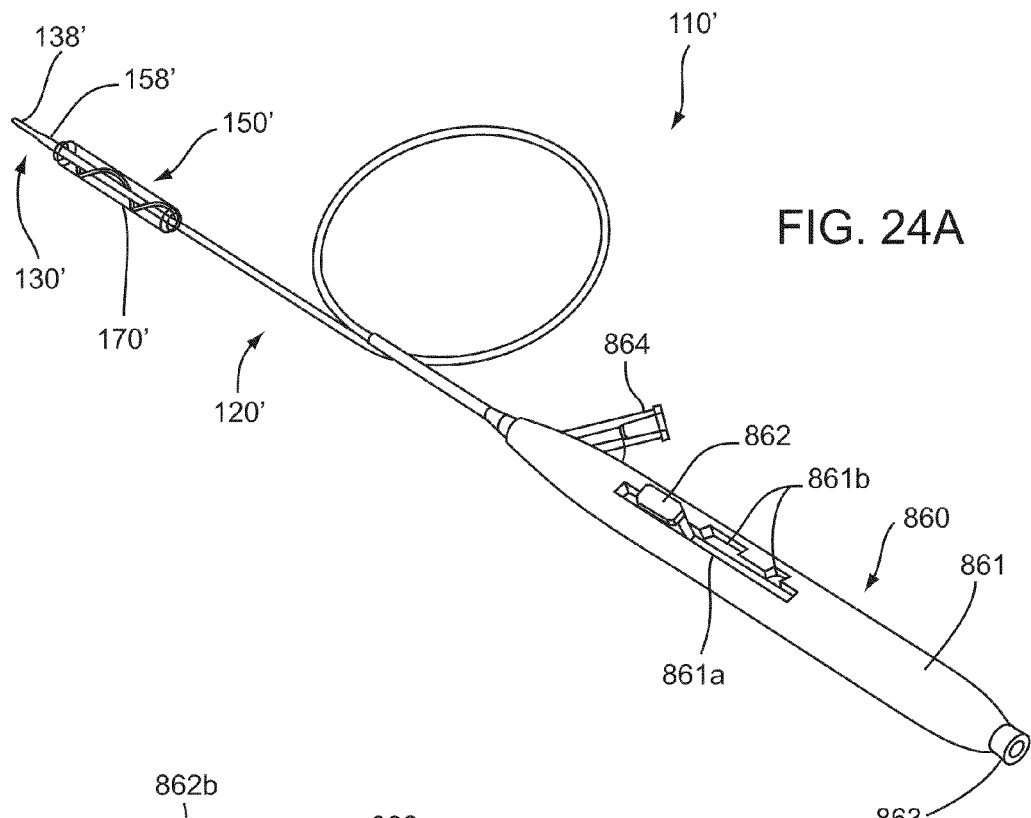
FIG. 24A is a perspective view of another apparatus, similar to that shown in FIG. 7, including a second exemplary embodiment of a handle for actuating the apparatus.
Figure 24B:
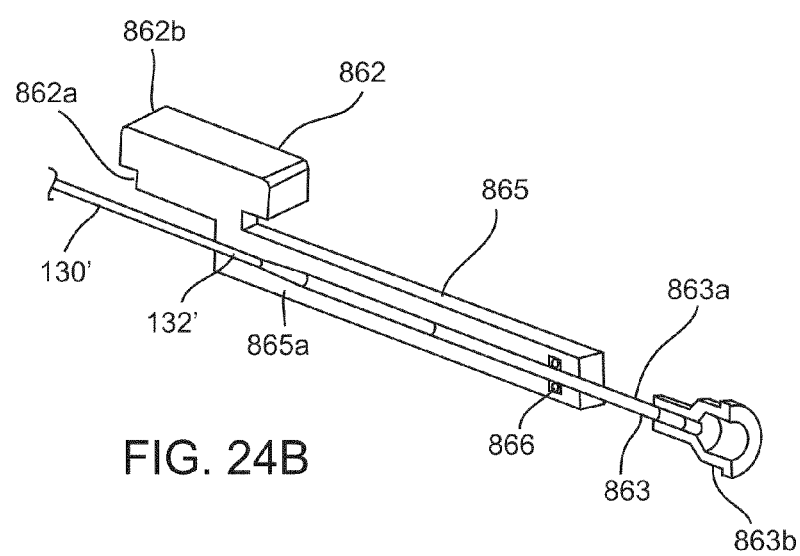
FIG. 24B is a cross-sectional detail of components of a slider control on the handle of FIG. 24A with a housing of the handle removed to show internal components.
Figure 24C:
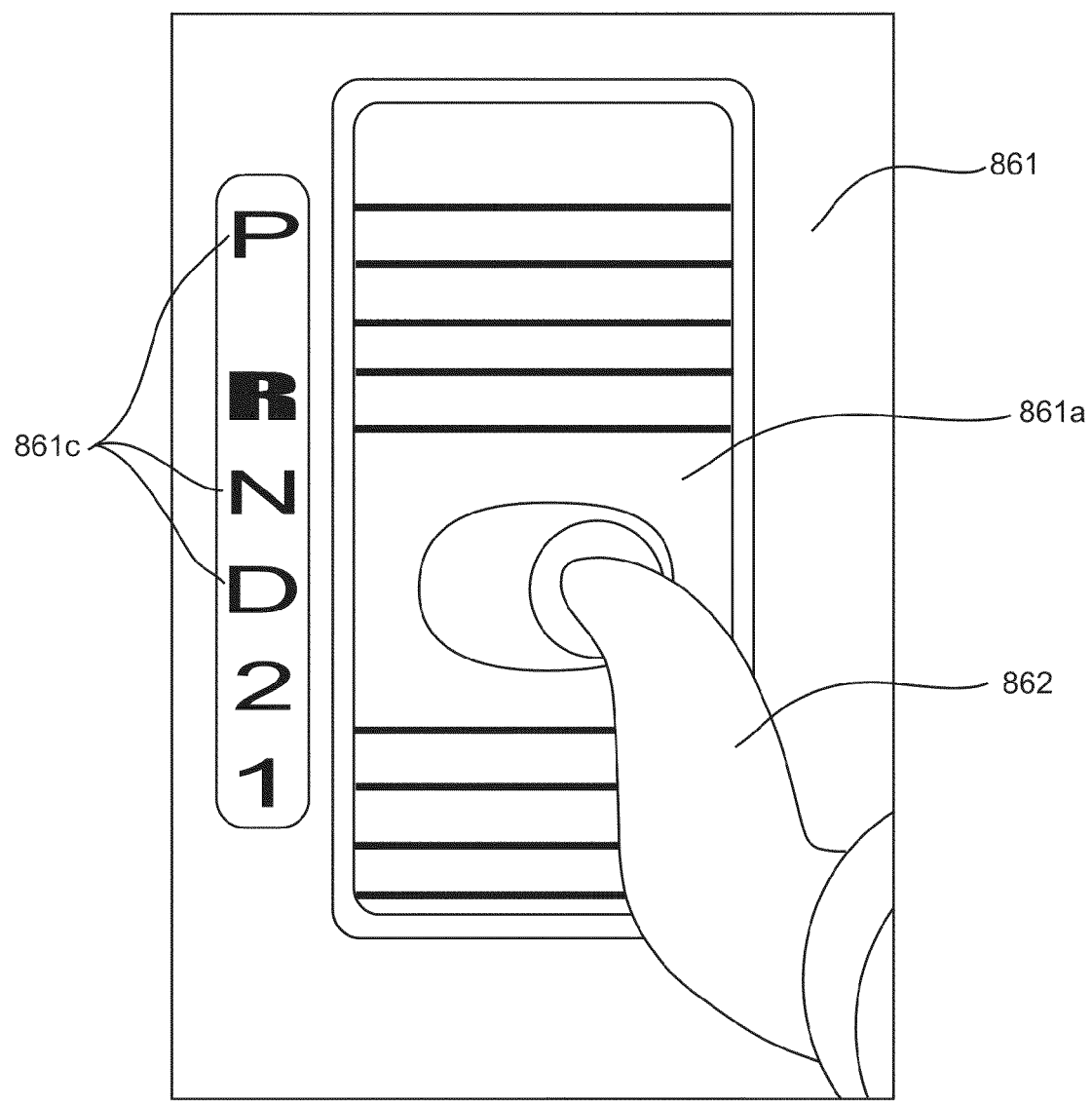
FIG. 24C is a detail of an alternate slider control, similar to that shown in FIGS. 24A and 24B, including visual indicators identifying actuatable positions of the apparatus.

Turning to FIGS. 24A-24C, another embodiment of a handle 860 is shown that includes an outer housing 861 with a side port 864 (shown in FIG. 24A), an inner carriage 865 (shown in FIG. 24B) slidable axially within the housing 861, and a hub 863 extending from the housing 861, generally similar to the handle 760. For example, the housing 861 may include one or more pieces, e.g., one or more sets of mating halves or clamshells (not shown) that may be connected together and may include a slot, track or other features (not shown) that allows the carriage 865 to slide axially within the housing 861, e.g., without substantial lateral movement. The housing 861 and/or carriage 865 may include one or more features that limit axial movement of the carriage 865 relative to the housing 861, e.g., to limit movement of the inner member 130' between the first position (for infusion from the outlet 158'), second position (for balloon inflation), and the third position (where the balloon 150' is directed to an expanded helical shape, not shown).

The proximal end 132' of the inner member 130' is substantially fixed relative to the carriage 865, e.g., by fixing the proximal end 132' in a passage 865a adjacent to a distal end of the carriage 865, for example, bonding with adhesive, sonic welding, fusing, interference fit, mating connectors (not shown), and the like. Thus, axial movement of the inner member 130' may be coupled to movement of the carriage 865.

The hub 863 may include a hypotube or other tubular member 863a and a Luer lock or other connector 863b secured to one another and/or to the outer housing 861. For example, a proximal end of the tubular member 863a and/or the connector 863b may be attached to a proximal end of the housing 861, e.g., by bonding with adhesive, sonic welding, fusing, interference fit, mating connectors (not shown), and the like.

The tubular member 863a may be slidably received in the passage 865a, e.g., adjacent a proximal end of the carriage 865, such that the tubular member 863a and connector 863b remain stationary relative to the housing 861 (and inner member proximal end 132') as the carriage 865 is directed axially. With both the tubular member 863a and inner member proximal end 132' received in the passage 865a, a guidewire or other instrument, backloaded through the inner member 130' may pass freely through the passage 865a, tubular member 863a, and out the connector 863b (or inserted through the connector 863b into the inner member 130'). One or more seals, e.g., o-ring 866, may be provided within or around the passage 865a that allow the tubular member 863 to slide therethrough while providing a fluid-tight seal that prevents fluid from leaking through the passage 865a out of the housing 861.

Instead of a rotary knob 762, the handle 860 includes a push button 862 carried by the housing 861 and coupled to the carriage 865. For example, the housing 861 may include an elongate slot 861a and the push button 862 may be slidable axially within the slot 861a. Optionally, as shown, the slot 861a may include one or more pockets or detents 861b that may capture the push button 862, e.g., to releasably secure the push button 862, and consequently the carriage 865 and inner member 130,' in one or more positions.

Optionally, the housing 861 may include one or more visual indicators, e.g., for identifying the position of the inner member 132' when the push button 862 is received in a particular pocket 861b. For example, as shown in FIG. 24C, the housing 861 may include numbers or other symbols 861c aligned with respective pockets (not shown) such that when the push button, in this embodiment, lever 862 is aligned with a particular symbol 861c, the user can confirm that the inner member 130' is in a respective particular position.

As best seen in FIG. 24B, the push button 862 may include a base 862a substantially fixed relative to the carriage 865 and a cap 862b slidable laterally relative to the base 862a. For example, the base 862a may be integrally molded or otherwise formed with the carriage 865 and the cap 862b may be attached to the base 862a such that the cap 862b may be slid laterally, e.g., substantially perpendicular to the longitudinal axis of the handle 860. For example, the cap 862b may be biased such that the cap 862b may automatically slide into a pocket 861b with which the cap 862b is aligned, yet the bias may be overcome to move the cap 862b out of the respective pocket 861b into the slot 861a so that the cap 862b may be slid axially into another pocket 861b. For example, a spring or other biasing mechanism (not shown) may be provided within the cap 862b or housing 861 that may push the cap 862b laterally from the base 862a.

Alternatively, the entire push button 862 may be fixed relative to the carriage 865, e.g., integrally molded or formed together, and the push button 862 and carriage 865 may be pivoted about the longitudinal axis to allow the cap 862b to be directed out of a particular pocket 861b, directed axially along the slot 861a, and released or otherwise placed in another pocket 861b. In this alternative, a spring or other biasing mechanism (not shown) may bias the push button 862 and carriage 865 to direct the cap 862b into any pocket 861b with which the cap 862b is aligned when the cap 862b is released.

In an exemplary embodiment, the handle 860 may include three pockets 861b, e.g., one corresponding to the first position of the inner member 130,' one corresponding to the second position, and one corresponding to the third position. Thus, to place the inner member 130' in any of the first, second, or third positions, the cap 862b may be directed out of a pocket within which the cap 862b is received, the push button 862 may be slid axially along the slot 861a, and released or otherwise directed into the desired pocket 861b. Alternatively, the handle 860 may include only one or two pockets 861b, e.g., if the push button 862 is biased axially to one of the positions.

During use, the push button 862 may be directed axially in a first direction, e.g., distally to the indicator "R" in FIG. 24C, and released or captured in a corresponding pocket, thereby translating the inner member 130' distally to the first position to open the outlet 158.' Thus, fluid delivered through the outer member 120' may pass through the balloon 150' and exit the outlet 158,' as described above. The push button 862 may be directed out of the pocket and directed axially, e.g., proximally, to the indicator "N", thereby translating the inner member 130' proximally to the second position, e.g., until the sealing member 138' seals the outlet 158' to allow balloon expansion. In addition, if desired, the push member 872 may be directed out of the "N" pocket, axially within the slot 861a, and released in the third pocket, corresponding to indicator "D," thereby translating the inner member 130' to the third position, e.g., to expand the balloon 150' to the expanded helical shape, also as described above.

Turning to FIGS. 25A and 25B, still another embodiment of a handle 960 is shown that includes an outer housing 961 including a side port 964 (shown in FIG. 25A), a carriage (not shown) within the housing 961, and a hub 963 extending from the housing 961, generally similar to the previous embodiments. The carriage may include a rack 965 (shown in FIG. 25B) including a plurality of teeth 965a spaced apart axially along the rack 965.

The proximal end (not shown) of the inner member 130' may be substantially fixed relative to the carriage (not shown) such that axial movement of the inner member 130' is coupled to movement of the carriage and consequently to the rack 965, similar to the previous embodiments.

The hub 963 may include a hypotube or other tubular member (not shown) and a Luer lock or other connector 963b secured to one another and/or to the outer housing 961, similar to the previous embodiments. The tubular member may be slidably received in a passage in the carriage, e.g., such that the connector 963b remains substantially stationary relative to the housing 961 (and inner member 130') as the carriage is directed axially.

In this embodiment, the actuator is a rotary wheel 962 rotatably mounted to the housing 961, as shown in FIG. 25A. The rotary wheel 962 includes an outer wheel 962a including ridges or other features to facilitate engaging and/or rotating the rotary wheel 962, and a pinion 962b that extends into the housing 961. As best seen in FIG. 25B, teeth on the pinion 962b may interlock with the teeth 965a on the rack 965 such that rotation of the outer wheel 962a causes the rack 965, and consequently, the inner member 130,' to move axially relative to the housing 961 and outer member 120.' Optionally, the housing 961 may include one or more visual indicators, e.g., for identifying the position of the inner member 132' when the wheel 962a is rotated to one or more orientations, similar to the previous embodiments.

During use, the rotary wheel 962 may be rotated in a first direction, e.g., to translate the inner member 130' distally to the first position to open the outlet 158.' When desired, the rotary wheel 962 may be rotated in a second opposite direction to translate the inner member 130' proximally to the second position and/or third position, e.g., to allow inflation of the balloon 150' and/or expanding the balloon 150' and helical member 170' to the expanded helical shape, similar to the previous embodiments. One advantage of the rotary wheel 962 is that the ratio of the outer wheel 962a, pinion 962b, and teeth 965 on the rack 965 may be designed to provide a desired mechanical advantage and/or precision of movement of the inner member 130.'

Figure 26A:
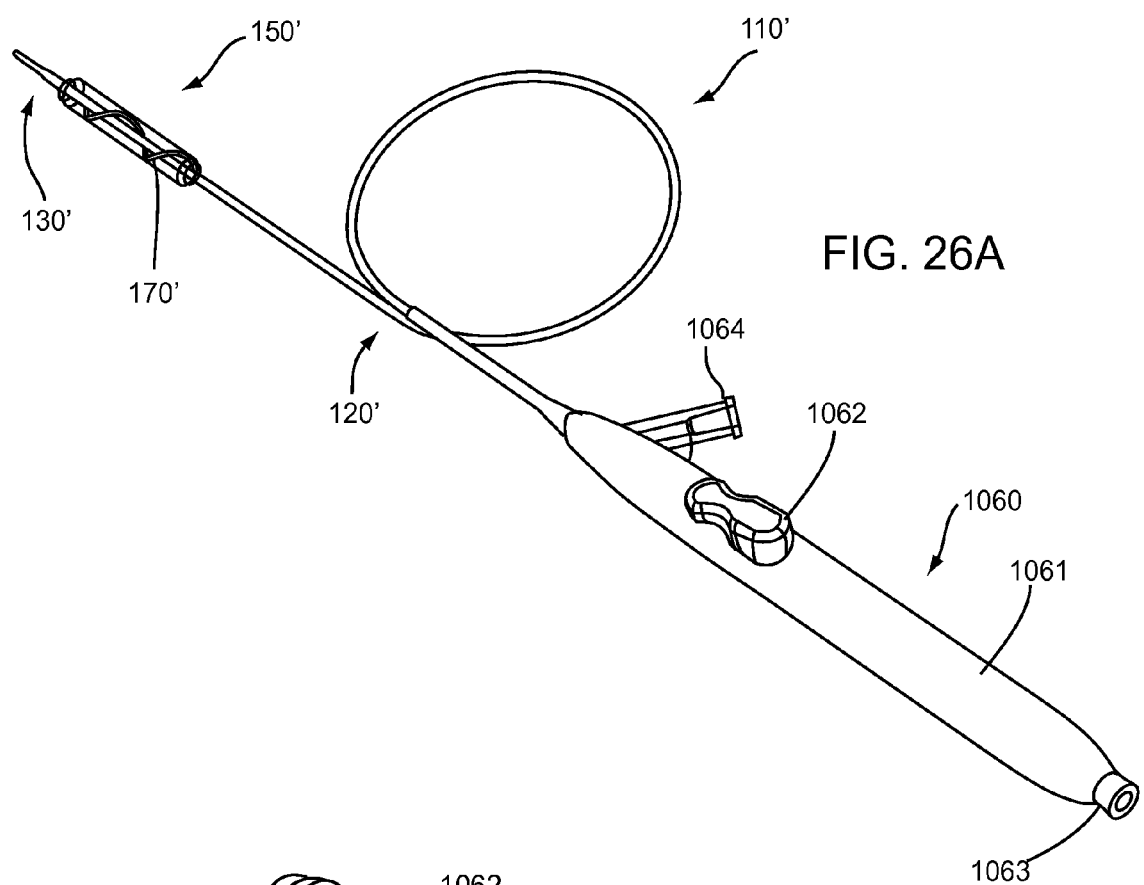
FIG. 26A is a perspective view of still another apparatus, similar to that shown in FIG. 7, including a fourth exemplary embodiment of a handle for actuating the apparatus.
Figure 26B:
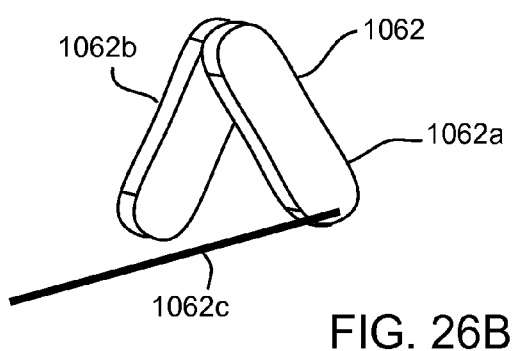
FIG. 26B is a cross-sectional detail of components of a squeeze control on the handle of FIG. 26A with a housing of the handle removed to show internal components.

Another embodiment of a handle 1060 is shown in FIGS. 26A and 26B that may be included in any of the apparatus shown herein. Similar to the previous embodiments, the handle 1060 includes a housing 1061 including a hub 1063 and a side port 1064. In this embodiment, the actuator is a squeeze button 1062 that may be depressed to direct the inner member 130' axially. e.g., from a first position to a second position, similar to the embodiments described elsewhere herein. Generally, when the squeeze button 1062 is pressed inwardly, links 1062a, 1062b defining the button 1062 are flattened out, thereby directing the proximal link 1062a proximally if the distal link 1062b is fixed axially relative to the housing 1061.

For example, a first end of the distal link 1062b may be pivotally coupled to the housing 1061 and a second end pivotally coupled to a first end of the proximal link 1062. A second end of the proximal link 1062a may be slidable axially along the housing 861, e.g., within a slot or track (not shown). With the second end of the proximal link 1062a coupled to the inner member 130,' e.g., by a cable or other linkage 1062c, as the squeeze button 1062 is pressed inwardly, the proximal link 1062 pulls the inner member 130,' e.g., from a first position (with the outlet 158' open) to a second position (allowing the balloon 158' to be inflated and/or expanded to the expanded helical shape).

Optionally a cover (not shown) may be placed over the squeeze button 1062 to protect the user from catching anything between the links 1062a, 1062b. In addition or alternatively, the squeeze button 1062 may be provided on the top of the housing 1061 (as shown), e.g., to allow a user to actuate the squeeze button 1062 with their thumb, or on the bottom of the housing 1061 (not shown), e.g., to allow a user to actuate the squeeze button 1062 with their index finger. Optionally, the handle 1060 may include one or more features (not shown) to allow the squeeze button 1062 to be releasably secured at one or more positions before the links 1062a, 1062b are completely flattened, e.g., to allow the inner member 130' to be translated and fixed in different positions, e.g., successively in the second and third positions, similar to the previous embodiments.

Figure 8:
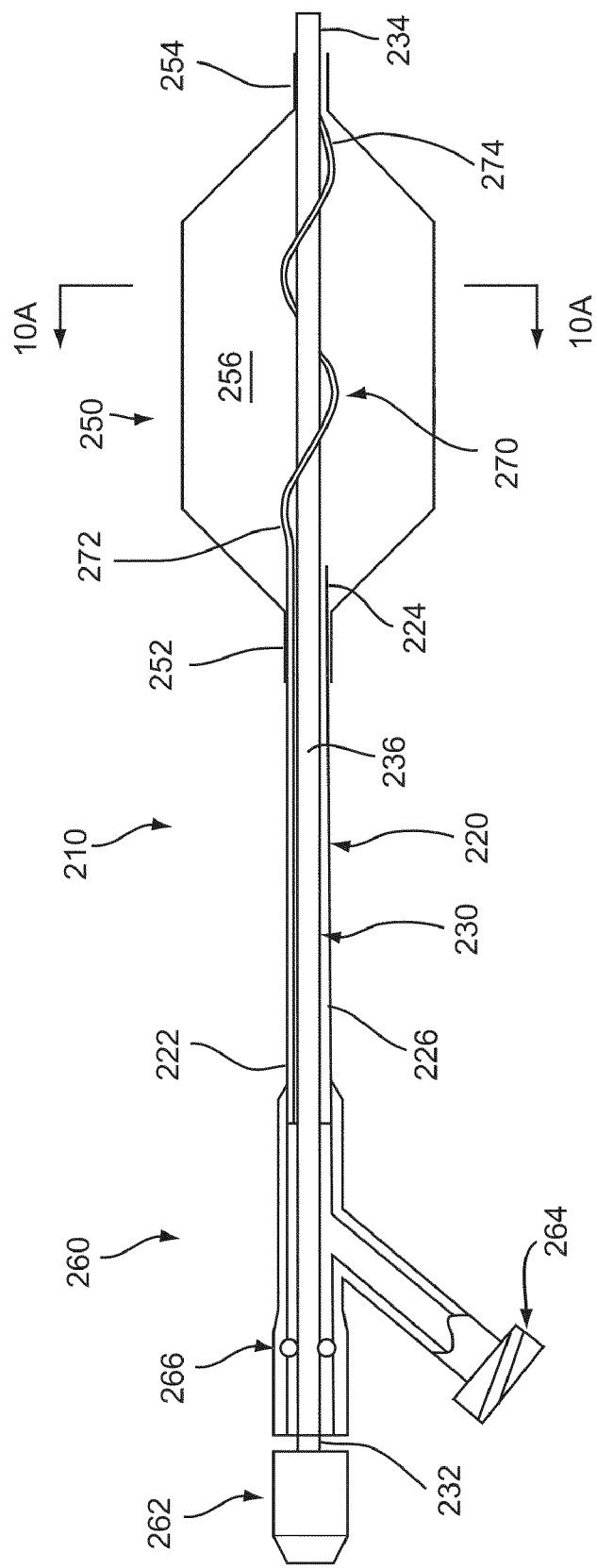
FIG. 8 is a side view of a third exemplary embodiment of an apparatus including a balloon for treating a body lumen, the apparatus operable in a first mode for dilating an obstruction within the body lumen, and a second mode for removing material within the body lumen.

Turning to FIG. 8, still another embodiment of an apparatus 210 is shown for treating a body lumen that generally includes an outer tubular member 220, an inner member 230, and an expandable balloon 250, and helical member 270 carried by the inner and/or outer members 220, 230, similar to the previous embodiments, but does not include a valve for opening or closing an outlet in the balloon, unlike the embodiment of FIG. 7. The apparatus 110 may be operable in a first mode for dilating an obstruction within a body lumen, and/or a second mode for removing obstructive material within a body lumen, as described further below.

As shown, the outer member 220 includes proximal and distal ends 222, 224, and a first lumen 226 extending therebetween, and the inner member 230 also includes proximal and distal ends 232, 234, and a second lumen 236 extending therebetween. The inner member 230 is sized to be slidably received within the first lumen 226 of the outer member 220, e.g., such that an annular space is defined between the outer and inner members 220, 230 for passing one or more fluids therethrough, also similar to the previous embodiments.

A handle or hub 260 may be coupled to or otherwise provided on the proximal end 222 of the outer member 220, e.g., including a pull handle or other actuator 262 for moving the inner member 230 relative to the outer member 220, a side port 264 for coupling one or more fluid sources to the apparatus 210, and an o-ring or other seal 166 between the outer and inner members 220, 230, which may also be similar to the previous embodiments.

The balloon 250 includes a proximal end 252 coupled to the outer member distal end 224, a distal end 254 coupled to the inner member distal end 234, e.g., attached by bonding with adhesive, interference fit, sonic welding, fusing, and the like, similar to the previous embodiments. The balloon 250 may be formed from substantially inelastic material, e.g., to provide a non-compliant balloon that expands to a predetermined size when inflated independent of pressure, or alternatively, the balloon 250 may be formed from elastic material, similar to the other embodiments described elsewhere herein.

Also similar to the embodiment of FIG. 7, the helical member 270 is coupled between the outer and inner members 220, 230. Thus, the helical member 270 may be movable from a relatively low profile, such as that shown in FIG. 8, to an expanded helical shape, as described further below with reference to FIGS. 9A-9D. As shown in FIG. 8, a first end 272 of the helical member 270 may be attached or otherwise secured directly to the distal end 224 of the outer member 220 and a second end 274 of the helical member 270 may be attached or otherwise secured to the distal end 234 of the inner member 230 adjacent the balloon distal end 252.

Figure 9A:
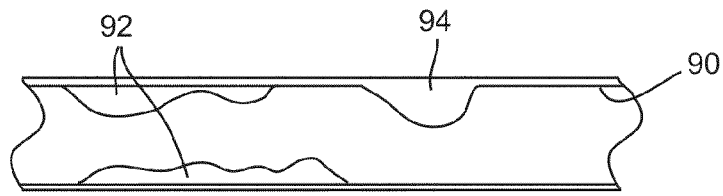
FIGS. 9A-9G are cross-sections of a body lumen showing exemplary methods for removing thrombus or other obstructive material from the body lumen and/or for dilating an obstruction within the body lumen using the apparatus of FIG. 7 or 8.

During use, in the exemplary methods shown in FIGS. 9A-9G, the apparatus 210 may be used for treating a body lumen 90, e.g., for removing obstructive material 92 and/or dilating an obstruction 94 within a body lumen 90, e.g., as shown in FIG. 9A. Similar to the previous embodiments, the target body lumen 90 may be a blood vessel, e.g., a vein or artery, a graft, e.g., an aorto-venous fistula, tubular xenograft, or synthetic tubular graft, and the like.

Optionally, the body lumen may be accessed using one or more additional instruments (not shown), which may be part of a system or kit including the apparatus 210, e.g., including one or more introducer sheaths, guide catheters, and/or guidewires (not shown). For example, to facilitate directing the apparatus 210 from an entry site to the target body lumen, a guide catheter, micro-catheter, introducer sheath, or other tubular body (not shown) may be placed from the entry site to the body lumen 90 using conventional methods. In addition or alternatively, a guidewire (not shown) may be placed from the entry site to the body lumen 90 if desired.

Figure 9B:
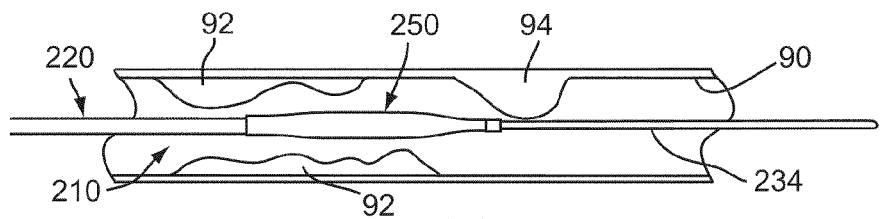

Initially, with reference to FIG. 9B, the apparatus 210 may be advanced into the body lumen 90 with the inner member 230 in the first or distal position, e.g., such that the balloon 250 is substantially collapsed. Optionally, contrast or other fluid may be delivered into the body lumen 90, e.g., via the second lumen 236 in the inner member 230 (not shown, see FIG. 8) or via a separate lumen (not shown) in the outer member 220. Markers (not shown) on the apparatus 10 may facilitate positioning the balloon 250 relative to the material 92 intended to be removed, e.g., to position the balloon 250 beyond or otherwise adjacent the material 92.

Optionally, the apparatus 210 may be introduced through a guide catheter or other tubular member (not shown), that includes a lumen communicating with a source of vacuum. With the balloon 250 disposed beyond the guide catheter, the source of vacuum may be activated to aspirate material within the body lumen 90, e.g., as the material 92 is dislodged or otherwise removed by the balloon 250, as described below.

Figure 9C:
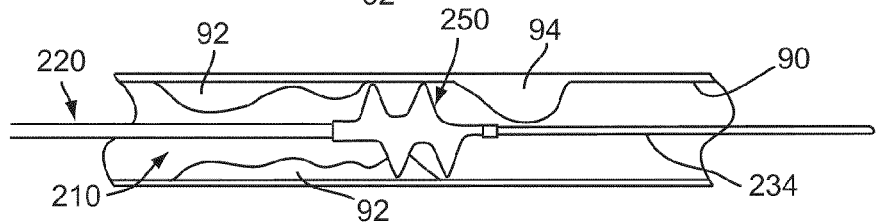
Figure 9D:
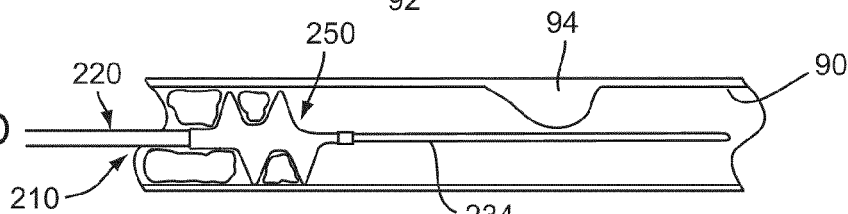

Turning to FIG. 9C, the inner member 230 may be directed proximally relative to the outer member 220, thereby causing the helical member 270 and consequently the balloon 250 to expand towards the expanded helical shape, as described above. As shown in FIG. 9D, the entire apparatus 210 may then be retracted to remove the material 92, e.g., scraping, scrubbing, or otherwise separating material that may be adhered to a wall of the body lumen 90. For example, the apparatus 210 may be pulled to remove the material 92 from the body lumen and into the lumen of the guide catheter, where the material 92 may be aspirated from the patient's body. Alternatively, the material 92 may be released in a manner that the material 92 may be metabolized naturally by the patient's body.

If desired, the inner member 230 may be returned to the first position to collapse the balloon 250, and the apparatus 210 moved to another location within the body lumen 90. The inner member 230 may be directed between the first and second positions as often as desired to expand the balloon 250 and separate or otherwise remove sufficient material 92.

Figure 9E:
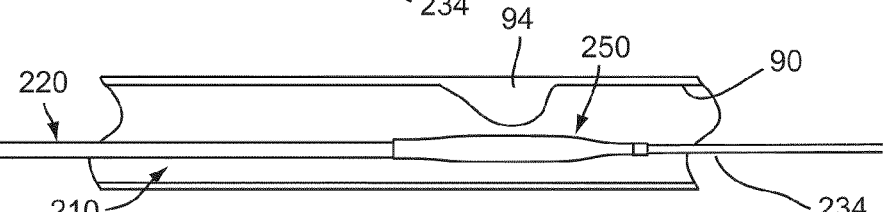
Figure 9F:
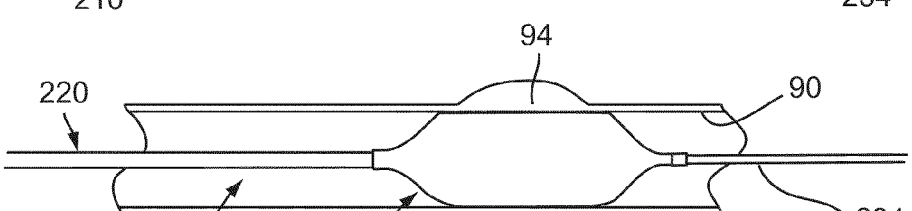
Figure 9G:
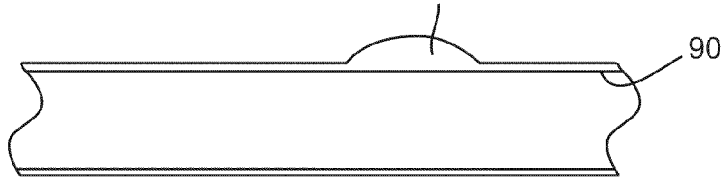

Turning to FIG. 9E, with sufficient material 92 removed, a stenosis, lesion, or other obstruction 94 is identified within the body lumen 90. The apparatus 210 may be reintroduced or repositioned in the body lumen 90 with the balloon 250 collapsed until the balloon 250 is positioned adjacent the obstruction 94, e.g., using fluoroscopy or other additional imaging. Once properly positioned, as shown in FIG. 9F, the balloon 250 may be inflated to dilate and/or otherwise treat the obstruction 94. Optionally, the balloon 250 may carry one or more diagnostic and/or therapeutic agents, which may be delivered against and/or into the obstruction 94 using the balloon 250. After sufficient treatment, the balloon may be deflated, and the apparatus 10 removed from the body lumen 90, as shown in FIG. 9G.

Optionally, with any of the embodiments described herein, various balloon configurations may be provided. For example, turning to FIG. 10A, with additional reference to the apparatus 250 of FIG. 8, an exemplary cross-section of the apparatus 210, taken through the balloon 250, is shown. FIG. 10A shows the helical member 270 wound around the inner member 230 and surrounded by the expanded balloon 250. Thus, both the helical member 270 and the inner member 230 are disposed within the interior 256 of the balloon 250. One of the disadvantages of such a balloon 250 is that the wall must be relatively thick since it is difficult to predict which areas of the balloon wall are going to contact and scrape along a wall of a target body lumen.

FIGS. 10B-10D show alternative embodiments of balloon or tubular constructions that may be provided for any of the embodiments described herein. These constructions may be provided for a balloon capable of inflation or for a tubular member capable of expansion to an expanded helical shape without being inflated. Exemplary embodiments of such devices are disclosed in U.S. Pat. No. 4,762,130, the entire disclosure of which is expressly incorporated by reference herein.

For example, as shown in FIG. 10B, a balloon or tubular member 250' is shown that includes a first lumen 251' that receives the inner member 230 and a second lumen 253' that receives the helical member 270 therein. When the tubular member 250' and helical member 270 are compressed axially, the helical member 270 may expand radially outwardly away from the inner member 230, thereby directing surface region 280' radially outwardly away from the inner member 230 since the surface region 280' is furthest from the first lumen 251.' Thus, because the surface region 280' is likely to contact the wall of the body lumen when the tubular member 250' is expanded, the construction of the tubular wall may be varied to enhance scraping and/or other removal of obstructive material. For example, features may be integrally molded or otherwise formed in the wall of the tubular member 250,' e.g., that extend helically around the tubular member 250' adjacent the second lumen 253.'

As shown in FIG. 10B, the surface region 280' may include a plurality of grooves that provide edges 282' that may facilitate scraping adherent material from the wall of the target body lumen, e.g., by concentrating contact forces with the wall of the body lumen. In addition, the tubular wall opposite the surface region 280' may be relatively thin since this area of the wall is unlikely to contact the wall of the body lumen, which may allow an overall cross-section or profile of the tubular member 250' to be reduced. Alternatively, or in addition, if desired, different property materials may be used, e.g., harder elastomeric materials with relatively thinner wall thickness for the surface region 280' or elsewhere on the tubular member 250.'

Turning to FIG. 10C, another embodiment of a tubular member 250" is shown that includes a first lumen 251" that receives the inner member 230 and a second lumen 253" that receives the helical member 270 therein, and ridges or protrusions 282" along surface region 280" that will contact the wall of the body lumen when the tubular member 250" is expanded. In a further alternative, shown in FIG. 10D, a tubular member 250''' may be provided that includes a first lumen 251''' having convolutions molded or otherwise formed into the tubular wall and a second lumen 253,''' and ridges or protrusions 282.''' The convolutions may increase the circumferential length of the tubular wall, and therefore allow the wall to stretch to a greater radial dimension, yet still direct the surface region 280''' towards the wall of a body lumen being treated.

Figure 11:
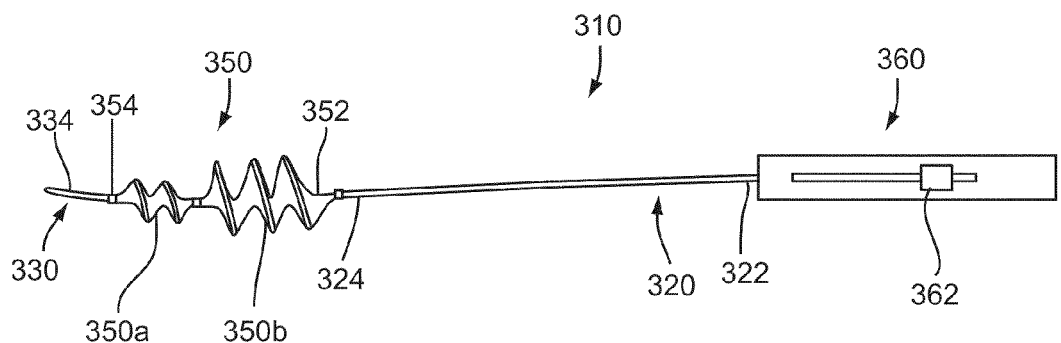
FIG. 11 is a side view of an alternative embodiment of the apparatus of FIG. 7 or 8, including an obstruction removal balloon having different size coils in different regions of the balloon.

Turning to FIG. 11, another embodiment of an apparatus 310 is shown that includes an outer member 320 including proximal and distal ends 322, 324, an inner member 330, and an expandable member 350 carried on distal ends 324, 334 of the outer and inner members 320, 330, and a handle 360 including an actuator 362, similar to the previous embodiments. Unlike the previous embodiments, the expandable member 350 may not include an interior coupled to a lumen extending through the outer member 320, i.e., the expandable member 350 may not be inflatable. However, alternatively, if desired, the apparatus 310 may include a lumen (not shown) extending through the outer member 320 and communicating with an interior of the expandable member 350 for selectively inflating or collapsing the expandable member 350. In addition, if desired, the apparatus 310 may include one or more sealing members or other valve (not shown) that may be opened or closed for selectively infusing fluid or inflating the expandable member 350, similar to the previous embodiments.

The expandable member 350 generally includes a proximal end 352 coupled to the outer member distal end 324 and a distal end 354 coupled to the inner member distal end 334, e.g., by bonding with adhesive, sonic welding, fusing, interference fit, one or more bands or other connectors (not shown), and the like. In addition, the apparatus 310 includes a helical member (not shown) that may also be coupled between the outer member and inner member distal ends 324, 334 and extend helically around the inner member 330 within the interior of the expandable member 350.

For example, the helical member may be loose within the interior of the expandable member 350. Alternatively, the helical member may be embedded in or otherwise attached to the wall of the expandable member 350, e.g., to an inner surface of the expandable member 350.

Unlike the previous embodiment, the helical member includes a first coil within a first region 350a of the expandable member 350 and a second coil within a second region 350b of the expandable member 350 having different properties. The first and second coils may be coupled to one another, e.g., integrally formed together as a single wire, filament, and the like, or may be formed as separate wires or filaments attached to one another. Each coil includes a plurality of turns that extend helically around the inner member 330, e.g., between the proximal and distal ends 352, 354 of the expandable member 350.

The coils may be provided in a relatively low profile around the inner member 330, e.g., when the inner member 330 is extended distally relative to the outer member 320 to a first position. When the inner member 330 is retracted proximally from the first position towards a second position, the coils may be compressed axially, thereby causing the coils to expand radially outwardly and expand the expandable member 350 radially outwardly to an expanded helical shape, similar to the previous embodiments.

The coils may have different mechanical properties from one another, thereby causing the first and second regions 350a, 350b of the expandable member 350 to expand to different sizes and/or shapes in the expanded helical shape. For example, as shown in FIG. 11, the first region 350a may be expanded to a smaller diameter than the second region 350b. This may be achieved by forming the first coil from thinner, narrower, or otherwise more flexible material than the second coil. In addition or alternatively, the coils may be biased to different diameters such that when the inner member 330 is in the distal or first position, the coils may be constrained in the low profile, and when the inner member 330 is directed proximally towards the second position, the coils may resiliently expand radially outwardly to the diameters set into the coil material.

In addition or alternatively, the coils may be expandable sequentially, e.g., such that the first region 350a of the expandable member 350 may expand to the expanded helical shape before the second region 350b. For example, the first coil in the first region 350a may have less resistance to expansion than the second coil in the second region 350b, e.g., by forming the first coil from thinner, narrower, and/or otherwise more flexible material than the second coil. For example, the first coil may include a bare wire wound helically around the inner member 330, while the second coil may include the same or different wire wrapped in a section of tubing, a sleeve, and the like, which may increase resistance to expansion. Thus, when the inner member 330 is directed from the first position towards the second position, the compressive force may be applied initially to the first coil, thereby expanding the first coil and the first region 350a of the expandable member 350, until a predetermined threshold is achieved, whereupon the second coil may expand and expand the second region 350b of the expandable member 350.

In another alternative, a sleeve (not shown) attached to the inner member 330 may initially initial surround the second coil in the first position such that only the first coil is free to expand when initially compressed. When the inner member 330 is directed towards the second position, the second coil may become exposed from the sleeve, and then expand radially outwardly to the expanded helical shape.

Figure 12:
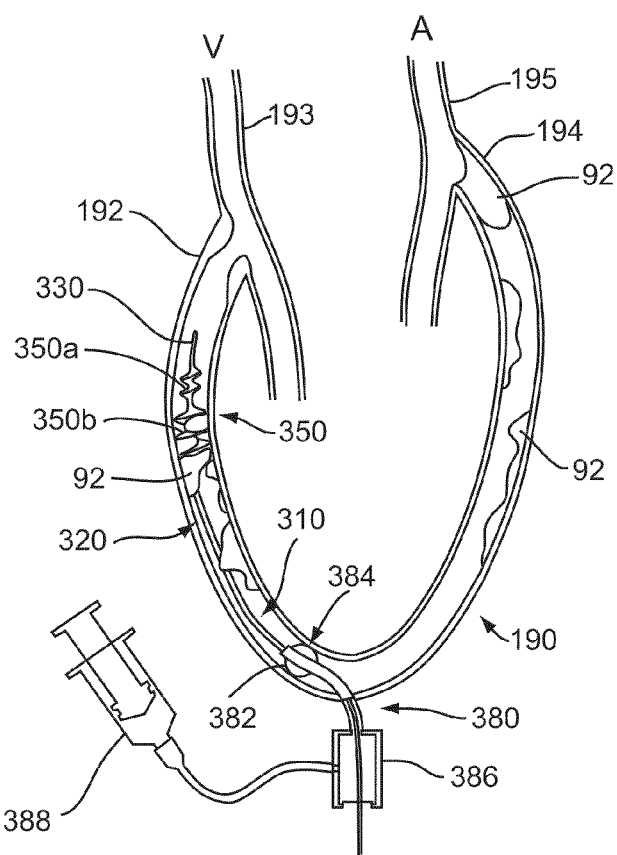
FIGS. 12 and 13 are cross-sectional views of a patient's body, showing methods for treating an arterio-venous dialysis graft using the apparatus of FIG. 11.
Figure 13:
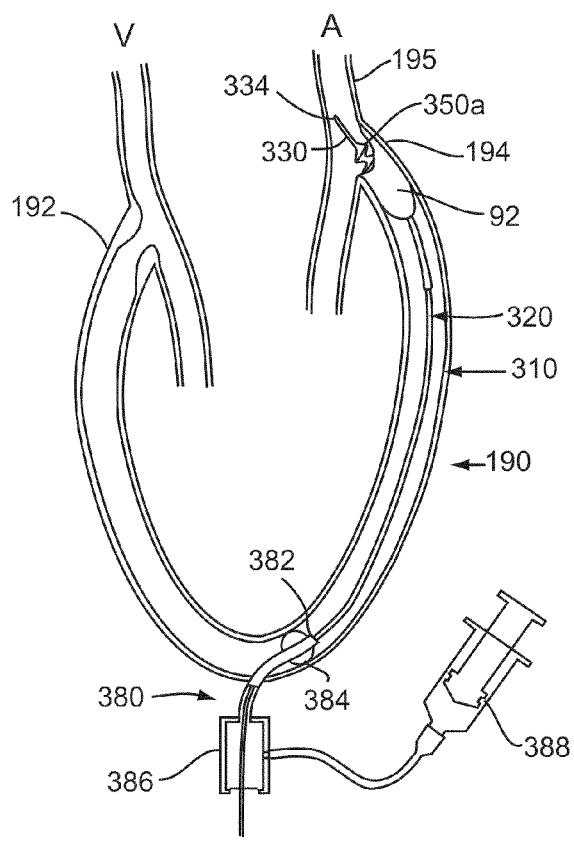

Turning to FIGS. 12 and 13, an exemplary method is shown for treating a body lumen, e.g., a arterio-venous dialysis graft 190, using the apparatus 310 of FIG. 11. As shown, the graft 190 includes a first or venous anastomosis 192 attached to a vein 193 within a patient's body, e.g., within the patient's arm, and a second or arterial anastomosis 194 attached to an artery 195 adjacent the vein 193. As shown, the graft 190 includes obstructive material 92, e.g., thrombus, plaque, and the like at multiple locations in the graft 190 including within each anastomosis 192, 194.

Initially, an introducer or guide sheath 380 may be placed within the graft 190, e.g., percutaneously through the patient's skin into a central region of the graft 190, using similar methods to those described elsewhere herein. The sheath 380 may include a distal end 382 having a size and/or shape for introduction into the graft 190 and a balloon 382 on the distal end 384 for substantially engaging a wall of the graft 190, e.g., to stabilize the sheath 380 relative to the graft 190 and/or to substantially seal the graft 190 from fluid flow between the ends 192, 194 of the graft 190. The sheath 380 may also include a reservoir 386 communicating with a lumen extending to an opening (not shown) in the distal end 382, and a source of vacuum 388, e.g., a syringe, for applying a vacuum to aspirate material from within the graft 190 during treatment.

The apparatus 310 may be introduced through the sheath 380 into the graft 190 with the expandable member 350 initially in a contracted condition. As shown in FIG. 12, the apparatus 310 may be advanced until the expandable member 350 is disposed distally beyond obstructive material 92 within the venous side of the graft 190, whereupon the inner member 330 (not shown) may be directed proximally to expand the expandable member 350 to the expanded helical shape. As shown, both coils have been expanded, thereby expanding both the first and second regions 350a, 350b of the expandable member 350, e.g., such that the second region 350b may substantially engage or otherwise contact the wall of the graft 190.

The apparatus 310 may then be withdrawn to scrape or otherwise separate adherent material 92 from the wall of the graft 190 and pull the material 92 towards the sheath 380. The source of vacuum 388 may be activated, if not already, to aspirate the material 92 through the sheath 380 into the reservoir 386. If desired, the inner member 330 may be advanced to collapse the expandable member 350 back towards the contracted condition and advanced further into the graft 190, e.g., to repeat the process of expanding the expandable member 350 to scrape or otherwise remove material 92.

Optionally, the sheath 380 may be repositioned within the graft 190 towards the arterial anastomosis 194, and the apparatus 310 reintroduced with the expandable member 350 in the contracted condition, e.g., to remove material 92 within the arterial side of the graft 190. Turning to FIG. 13, although material has been removed from the graft 190, additional obstructive material 92 remains within the arterial anastomosis 194. Because the anastomosis 194 communicates with the artery 195, care should be taken to ensure that material is not released into the artery 195, where the material may flow into tissue beds, cause ischemia, or other damage to tissue downstream of the artery 195.

The apparatus 310 may be advanced until the distal end 334 of the inner member 330 passes through material 92 within the arterial anastomosis 194 with the expandable member 350 in the contracted condition. At this point, the inner member 330 may be directed proximally sufficient distance to expand the first region 350a of the expandable member 350 without substantially expanding the second region 350b. The apparatus 310 may then be withdrawn to pull the expandable member 350 back towards the sheath 380, where any material 92 removed from the anastomosis 194 may be aspirated out of the graft 190. Thus, the smaller first region 350b may allow greater care to remove material from sensitive regions, while the second region 350b may be expanded within relatively large body lumens or otherwise when it is desired to apply greater force and/or remove greater amounts of material.

Figure 14:
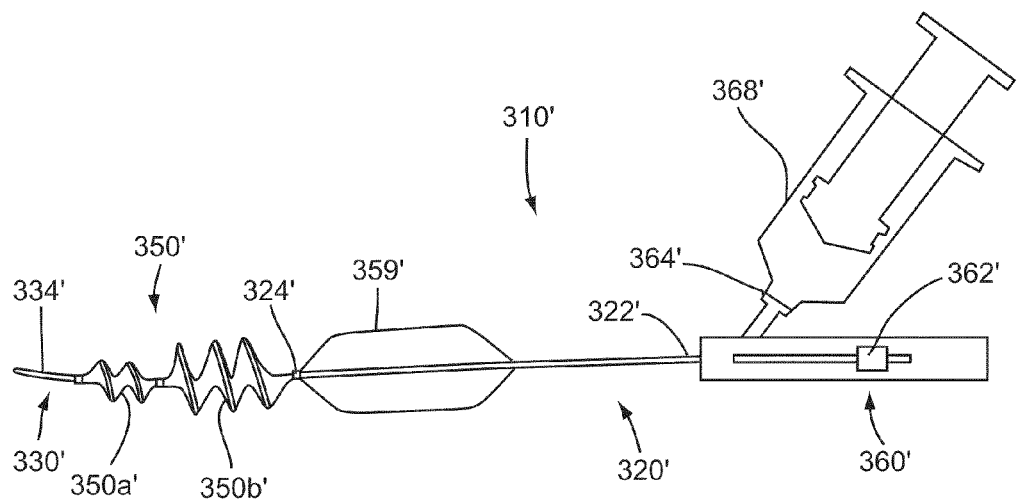
FIG. 14 is a side view of another alternative embodiment of the apparatus of FIG. 11, including a dilation balloon adjacent the obstruction removal balloon.

Turning to FIG. 14, an alternative embodiment of the apparatus 310 shown in FIG. 11 is shown. The apparatus 310' is generally the same as apparatus 310, e.g., including an outer member 320' including proximal and distal ends 322,' 324,' an inner member 330,' an expandable member 350' carried on distal ends 324,' 334' of the outer and inner members 320,' 330,' and first and second coils defining a helical member within the expandable member 350 including first and second regions 350a,' 350b,' similar to the previous embodiments. Unlike the previous embodiment, the apparatus 310' includes a dilation balloon 359,' e.g., a substantially non-compliant, high pressure balloon, on the outer member distal end 324.' In addition the apparatus 310' includes a handle 360' that includes an actuator 362' and a side port 364' to which a source of inflation media and/or vacuum 368' may be connected.

The apparatus 310' may be used similar to the apparatus 310 shown in FIG. 11, e.g., using the methods of FIGS. 12 and 13. In addition, the dilation balloon 359' may be positioned within a stenosis, lesion, or other obstruction, e.g., in the graft 190 of FIGS. 12 and 13, or within other body lumens. The balloon 359' may then be inflated or otherwise expanded to dilate the body lumen, similar to other embodiments described above. Optionally, a stent or other prosthesis (not shown) may be carried by the balloon 359,' e.g., such that the prosthesis may be implanted within a body lumen after using the balloon 350' to remove obstructive material from the body lumen. Alternatively, a stent or other prosthesis may be carried and delivered using any of the other embodiments described herein, e.g., on the balloon 150 or 250 of the apparatus 110 or 210, shown in FIG. 7 or 8.

Figure 15A:
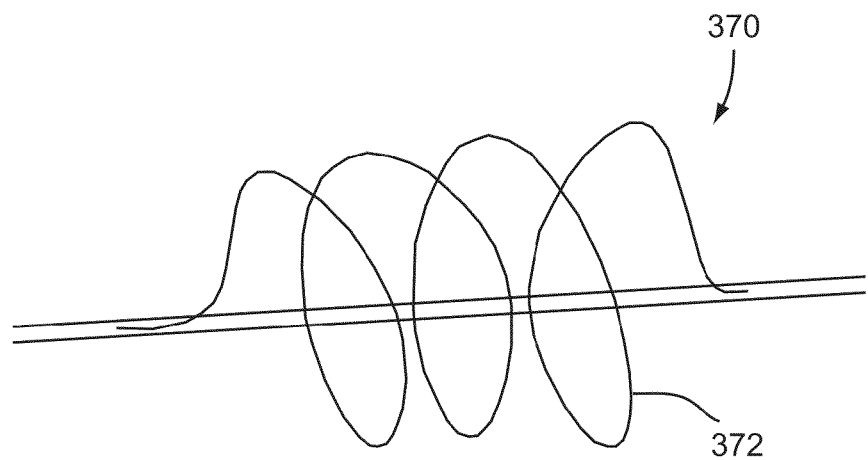
FIGS. 15A and 15B are alternative embodiments of coil structures that may be provided within the balloon of any of the apparatus of FIGS. 8-14.
Figure 15B:
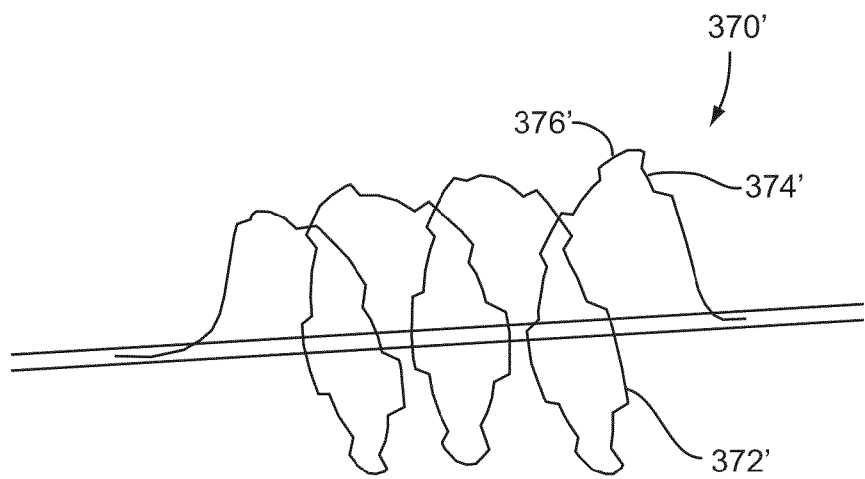

Turning to FIGS. 15A and 15B, exemplary embodiments of coils are shown that may be included in any of the apparatus described above including a helical member for expanding a balloon or other expandable member to an expanded helical shape. For example, FIG. 15A shows a coil 370 that includes substantially smooth, uniform turns 372 that may be incorporated as a helical member in any of the apparatus described above. Alternatively, as shown in FIG. 15B, a coil 370' may be provided that includes a plurality of turns 372' having alternating high points 374' and low points 376' that may increase contact force with a wall of a body lumen when the coil 370' is included within a balloon or expandable member (not shown), such as those described above. The high and low points 374,' 376' may be staggered between adjacent turns, e.g., to ensure that at least some high points 374' contact and/or scrape along substantially the entire circumference of a wall of a target body lumen.

Figure 16:
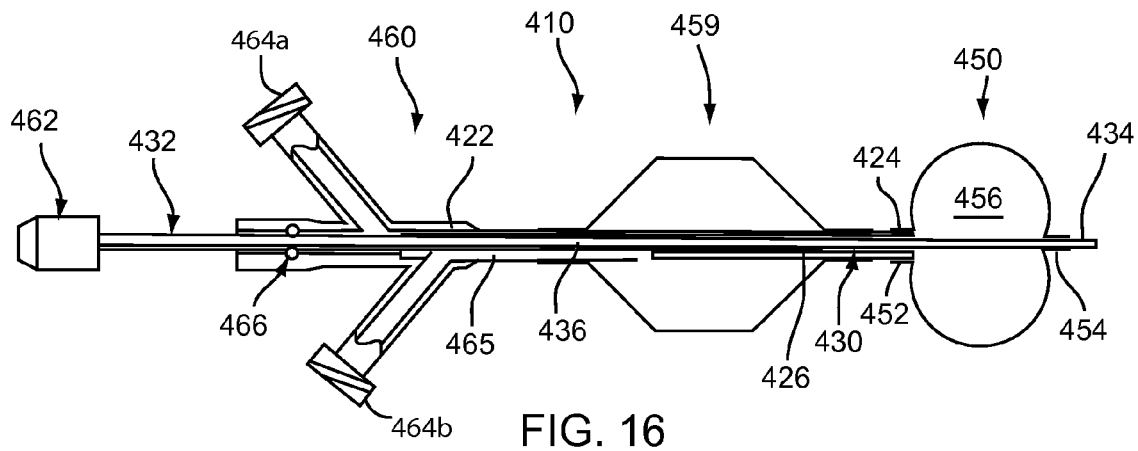
FIG. 16 is a side view of a fourth exemplary embodiment of an apparatus including a balloon for treating a body lumen, the apparatus operable in a first mode for removing material within the body lumen, and in a second mode for dilating an obstruction within the body lumen.

Turning to FIG. 16, still another embodiment of an apparatus 410 is shown that includes multiple expandable devices on a single shaft, e.g., such that the apparatus 410 may be operable in multiple modes, e.g., a first mode for removing material within a body lumen, and a second mode for dilating an obstruction within a body lumen.

Generally, the apparatus 410 generally includes an outer member 420, an inner member 430, a handle 460, and a first balloon or other expandable member 450 carried by the outer and inner members 420, 430 and including an interior 456, similar to the previous embodiments. The outer member 420 includes proximal and distal ends 422, 424, and a first lumen 426 extending therebetween, and the inner member 430 also includes proximal and distal ends 432, 434, and a second lumen 436 extending therebetween.

The first balloon 450 includes a proximal end 452 coupled to the outer member distal end 424 and a distal end coupled to the inner member distal end 434, and includes an interior communicating with the first lumen 426. The first balloon 450 may be formed from elastic material, e.g., such that the first balloon 450 may be expanded to a range of diameters and/or shapes, e.g., depending upon the volume of inflation media delivered into the interior of the first balloon 450 and/or the position of the inner member 430 relative to the outer member 420.

In addition, a second balloon 459 may be provided on the outer member 420, e.g., proximal to the first balloon 450. The second balloon 459 may be formed from substantially inelastic material, e.g., to provide a non-compliant, high pressure dilation balloon, similar to other embodiments described elsewhere herein. The outer member 420 includes a third inflation lumen 465 communicating with the interior of the second balloon 459.

As shown, the handle 460 includes a first side port 464a communicating with the first lumen 426 for delivering inflation media into the first balloon 450, and a second side port 464b communicating with the third inflation lumen 465 for delivering inflation media into the second balloon 459. In addition, the handle 460 may include a pull handle or other actuator 462 for directing the inner member 430 to one or more axial positions relative to the outer member 420, and one or more seals, e.g., o-ring 466 for sealing the first lumen 426, similar to the previous embodiments.

Figure 17A:
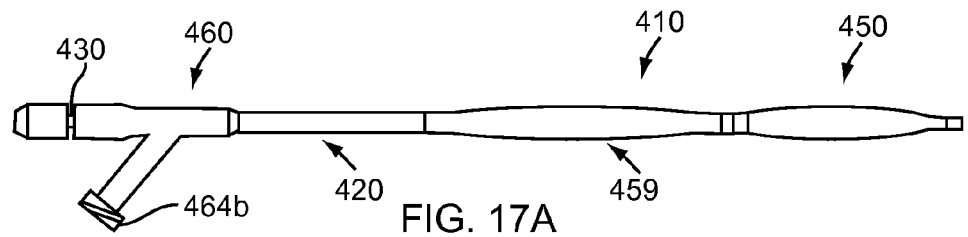
FIGS. 17A-17D are side views of the apparatus of FIG. 10, showing operation of the apparatus between an initial delivery configuration (FIG. 11A), the first mode for removing material within a body lumen (FIGS. 11B and 11C), and the second mode for dilating an obstruction within a body lumen (FIG. 11D).

Turning to FIGS. 17A-17D, the apparatus 410 is shown in different modes with the inner member 430 in respective positions. First, as shown in FIG. 17A, the inner member 430 is in a first or distal position with the first and second balloons 450, 459 in contracted conditions. In this configuration, the apparatus 410 may be introduced into a patient's body, into a target body lumen being treated, similar to the previous embodiments.

Figure 17B:
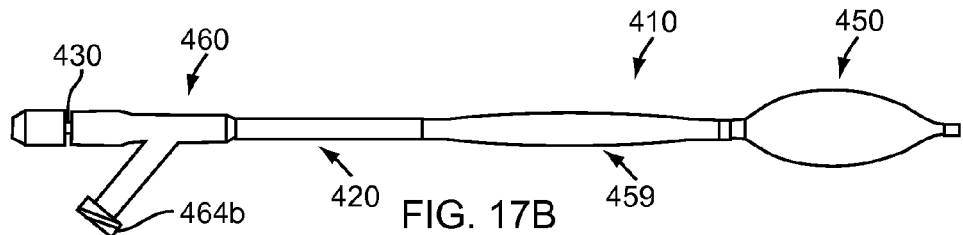
Figure 17C:
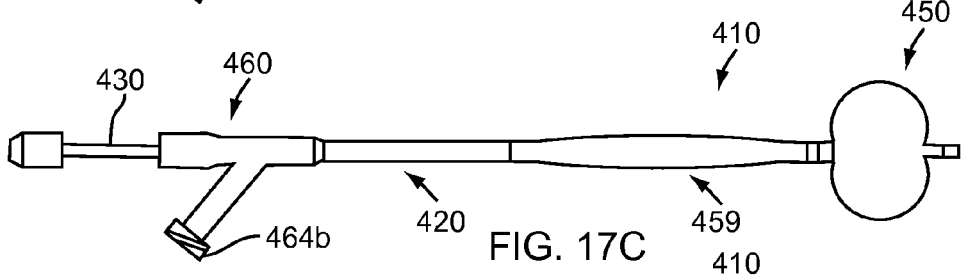

Turning to FIG. 17B, the first balloon 450 has been inflated to an expanded condition with the inner member remaining in the first position. Thus, the first balloon 450 may be expanded to one or more diameters, e.g., to engage or contact the wall of a body lumen being treated. The apparatus 410 may then be retracted or otherwise directed axially to scrape the first balloon 450 along the wall, e.g., to remove thrombus or other adherent material from the wall. Optionally, as shown in FIG. 17C, if greater pressure is desired, or a larger balloon is desired due to the size of the body lumen, the pull handle 462 may be directed proximally to pull the inner member 430 proximally relative to the outer member 420, thereby axially compressing and radially expanding the first balloon 450.

Figure 17D:
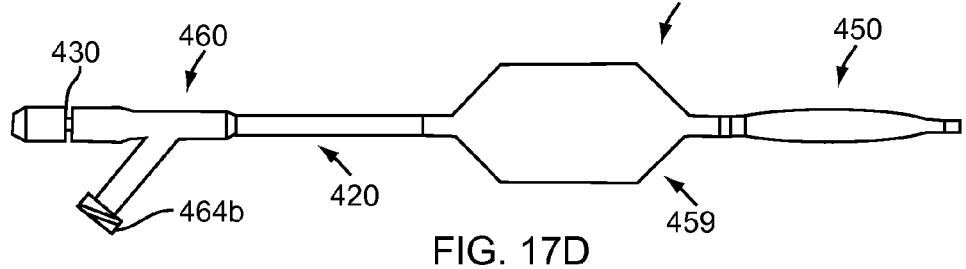

Finally, as shown in FIG. 17D, if it desired to dilate a stenosis, lesion, or other obstruction, the first balloon 450 may be collapsed to the contracted condition, and the second balloon 459 may be positioned adjacent the obstruction and inflated to expand and dilate the obstruction, similar to the previous embodiments. Thus, the apparatus 410 may be used to different treatments, e.g., embolectomy and/or angioplasty, without having to remove the apparatus 410, similar to the previous embodiments. The apparatus 410 may be tracked over a guidewire or other rail received through the second lumen 436 of the inner member 430, which may facilitate directing the apparatus 410 to various positions within a body lumen during treatment.

Figure 18:
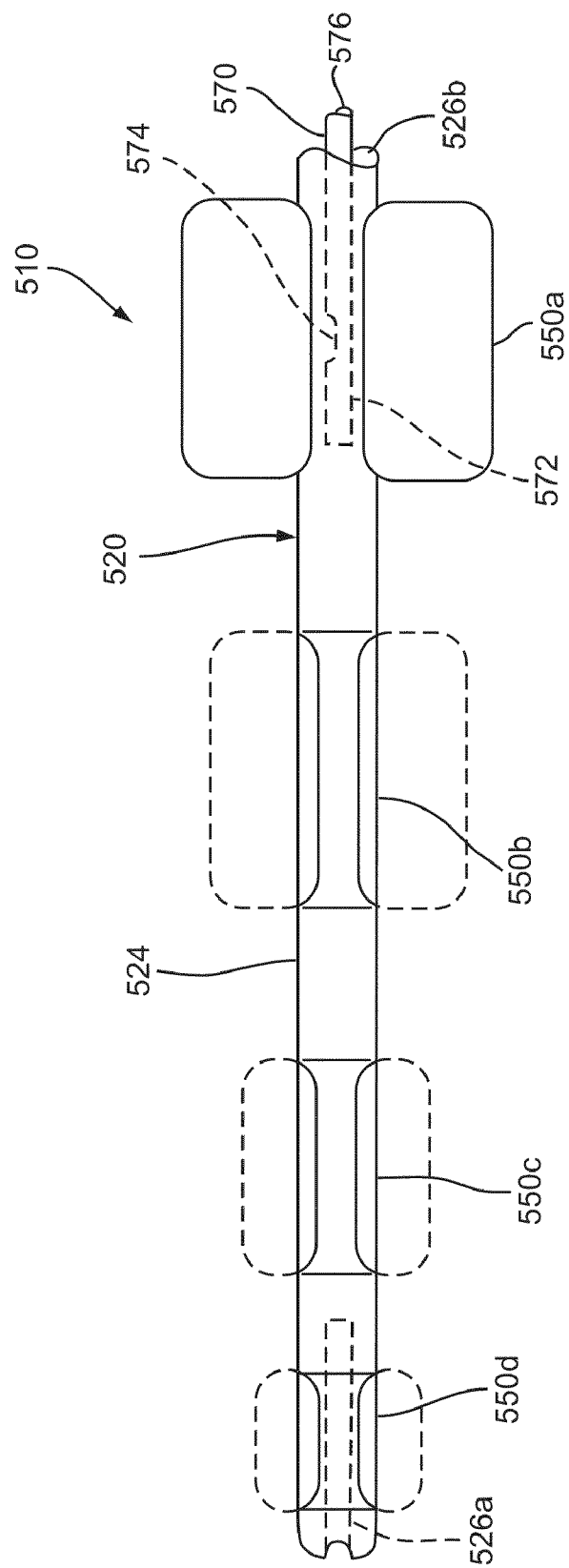
FIG. 18 is a side view of a distal end of another embodiment of a balloon catheter including a plurality of difference size balloons and a valve member for selectively delivering inflation media to one of the balloons.

Turning to FIG. 18, another embodiment of a balloon apparatus 510 is shown that includes a catheter body or other tubular member 520 including a proximal end (not shown), a distal end 524 sized for introduction into a body lumen, and a plurality of lumens 526 extending between the proximal end and the distal end 524. For example, the catheter body 520 may include a guidewire lumen 526a, e.g., sized for slidably receiving a guidewire or other rail (not shown) therethrough, such that the apparatus 510 may be advanced over a guidewire into a patient's body.

In addition, the catheter body 520 may include an inflation lumen 526b that may communicate with a source of inflation media and/or source of vacuum (not shown) connected to the proximal end of the catheter body 520. A plurality of balloons or other expandable members 550 are spaced apart on the distal end 524 that may be independently expandable. For example, the balloons 550 may be formed from substantially inelastic material, such that the balloons 550 may be expanded to a predetermined diameter. Thus, the balloons 550 may be non-compliant, high pressure dilation balloons, similar to the other embodiments described elsewhere herein.

For example, the balloons 550 may be configured such that the inflated diameter and/or length of the balloons 550 vary along the distal end 524 of the catheter body 520. As shown, in an exemplary embodiment, the first balloon 550a may be expandable to a diameter of seven millimeters (7 mm), the second balloon 550b to a diameter of six millimeters (6 mm), the third balloon 550c to a diameter of five millimeters (5 mm), and the fourth balloon 550d to a diameter of four millimeters (4 mm). Thus, during use, the fourth balloon 550d may be initially positioned within an obstruction and inflated to dilate the obstruction. If further dilation is needed, the fourth balloon 550d may be deflated, the third balloon 550c may be positioned with the obstruction, and inflated to further dilate the obstruction. Thus, each successive balloon may be used, if desired, to provide increasing dilation of an obstruction.

The interior of each of the balloons 550 may communicate with the inflation lumen 526b, i.e., such that the catheter body 520 includes only a single inflation lumen 526, which may reduce the overall profile of the catheter body 520. In order to selectively inflate one of the balloons 550, a valve member 570 may be provided within the inflation lumen 526b that may be positioned such that the inflation lumen or a lumen 576 within the valve member 570 communicates with an interior of only one of the balloons 550.

For example, as shown, the valve member 570 may include an outlet port 574 on a distal end 572 of the valve member 570 that may communicate with the valve member lumen 576. The valve member 570 may slidably but sealingly engage the catheter body 520, such that the outlet port 574 may be aligned with an interior of a respective balloon 526. Thus, when inflation media is delivered through the valve member lumen 576, the inflation media may exit the outlet port 574 and inflate only the balloon 526 with which the outlet port 574 is aligned. It will be appreciated that other valve arrangements may be provided for delivering inflation media into the balloons individually. For example, a valve member (not shown) may be rotatable within the inflation lumen 526b and may include one or more outlet ports that are aligned with passages (also not shown) into the interiors of respective balloons 550 when the valve member is in a predetermined angular orientation.

Turning to 19-21B, an exemplary embodiment of an apparatus 610 is shown for removing, retrieving, and/or otherwise capturing thrombus, objects, and/or obstructive material within a body lumen 90, such as a blood vessel, aorto-venous fistula, tubular graft, and the like. Generally, the apparatus 610 includes a catheter, sheath, or other tubular member 620, and an obstruction clearing or fragmentor device 640 including one or more fragmentor loops or elements 650 carried by a guidewire, shaft, or other elongate member 630.

Figure 19:
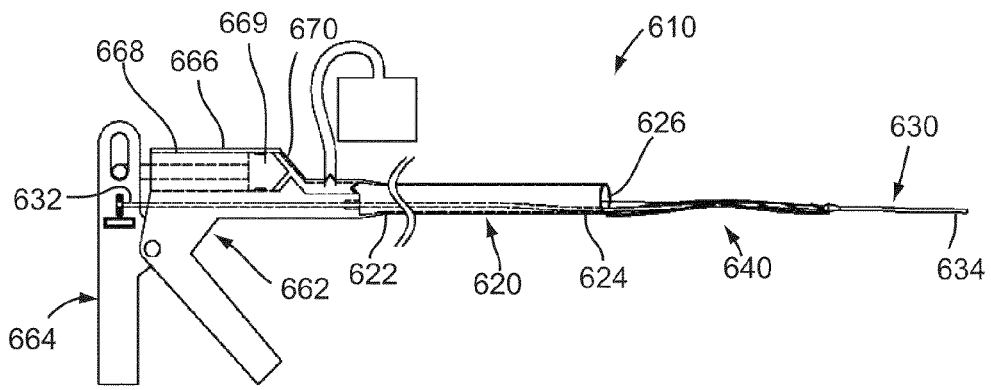
FIG. 19 is a side view of an exemplary embodiment of an apparatus for removing obstructive material within a body lumen.

As best seen in FIG. 19, the catheter 620 includes a proximal end 622, a distal end 624 sized for introduction into a body lumen, and a lumen 626 extending therebetween. The proximal end 622 is coupled to a handle 660 that includes an actuator for activating the fragmentor device 640 and/or other components of the apparatus 610. As shown, the handle 660 includes first and second handle portions 662, 664 that are movably coupled to one another, e.g., by pin, hinge, or other fulcrum 663, such that the second handle portion 662 may pivot or otherwise move relative to the first handle portion 662 to actuate the apparatus 610.

The first handle portion 662 includes a housing 666 (shown schematically in FIGS. 19 and 20) carrying various components of the apparatus 610 and to which the proximal end 622 of the catheter 620 is attached or otherwise coupled. For example, the housing 666 may include a piston assembly or other source of vacuum 668 including a piston 669 slidable within a chamber 670 and communicating with the lumen 626 of the catheter 620 via passage 671. The piston 669 may be coupled to the second handle portion 664 such that the piston 669 may be directed into and out of the chamber 670 during actuation of the second handle portion 664, e.g., to apply a vacuum to the catheter 620 lumen for aspirating material adjacent the catheter distal end 624. The housing 666 includes a reservoir 672 also communicating with the lumen 626 via passage 671. The piston assembly 668 may also provide positive pressure to expel fluid or other material within the passage 671 into the reservoir 672.

Figure 20:
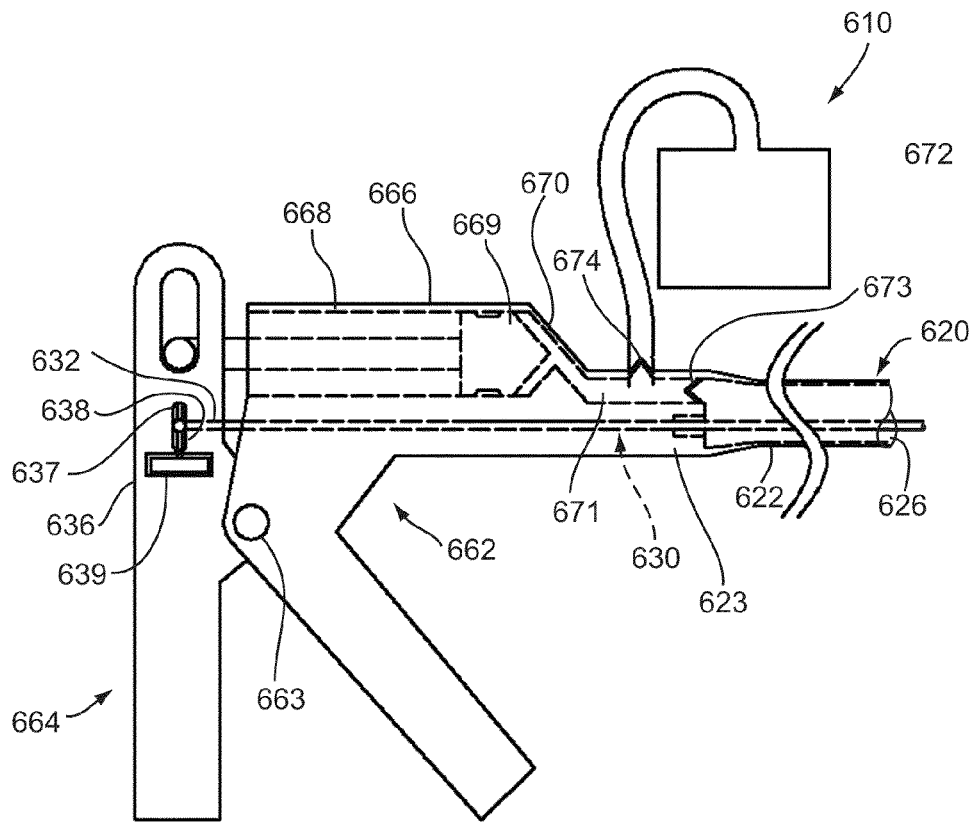
FIG. 20 is a detail of a handle of the apparatus of FIG. 19.

For example, as best seen in FIG. 20, a pair of one-way valves, e.g., duckbill or other check valves 673, 674, may be provided in the passage 671 for allowing flow of fluid or other material through the valves 673, 674 in only one direction. For example, inlet valve 673 may allow material to enter the passage 671 from the catheter lumen 626 without allowing substantial flow of material back into the lumen 626 from the passage 671. Outlet valve 674 may allow material to flow from the passage 671 into reservoir 672 without allowing substantial flow of material back into the passage 671.

Thus, when the piston 669 is drawn partially from the chamber 670, e.g., by actuation of the second handle portion 664, a vacuum may be created, opening the inlet valve 673 and creating a vacuum within the catheter lumen 626, thereby aspirating material from beyond the catheter distal end 624 through the lumen 626 into the passage 671. When the piston 669 is advanced back into the chamber 670, e.g., when the second handle portion 664 is released or reset, a positive pressure is created in the passage 671, the inlet valve 673 is closed and the outlet valve 674 is opened, thereby forcing material within the passage 671 into the reservoir 672.

Returning to FIG. 19, the guidewire 630 generally includes a proximal end 632 extending into the handle 660, e.g., coupled to the second handle portion 664, and a distal end extending from the lumen 626 of the catheter 620 distally beyond the distal end 624 of the catheter 620. A seal 623 may be provided in the handle 660, e.g., to accommodate movement of the guidewire 630 into and out of the handle 660 and catheter 620 while preventing fluid from leaking from within the lumen 626.

As best seen in FIG. 20, the proximal end 632 of the guidewire 630 may be coupled to an adjustment control 636, e.g., to adjust a distance the guidewire 630 is pulled when the second handle portion 664 is actuated. For example, as shown, the proximal end 632 of the guidewire 630 may be slidably received in a slot 637 and coupled to a jack screw 638. The jack screw 638 may be coupled to a control knob 639 such that rotation of the know causes the jack screw 638 to move the proximal end 632 of the guidewire 630 up or down in the slot 637.

As the proximal end 632 of the guidewire 630 is directed upwardly in the slot 637, the proximal end 632 becomes further from the fulcrum 663, thereby increasing the distance the proximal end 632 of the guidewire 630 moves when the second handle portion 664 is actuated and released. As the proximal end 632 is directed downwardly in the slot 637, the distance the proximal end 632 moves decreases when the second handle portion 664 is actuated and released. Movement of the proximal end 632 causes the distal end 634 of the guidewire 630 to move proximally and distally relative to the catheter distal end 624 for actuating the fragmentor device 640, as described further below.

Turning to FIGS. 20A and 20B, the fragmentor device 640 includes a pair of loops 650, although alternatively, the fragmentor device 640 may include additional loops, e.g., even numbers such that the loops may be coupled to the guidewire 630. As shown, a proximal edge of the first loop 650a is coupled to the catheter distal end 624 and an opposite distal edge is coupled to a proximal edge of the second loop 650b whose opposite distal edge is coupled to the guidewire 630, e.g., at hub 633. Each of these connections may be hinged, e.g., to allow the loops 650 to move proximally and distally during actuation. Optionally, the proximal edge of the first loop 650a may be hingedly coupled to the catheter distal end 624 at least partially within the lumen 626, e.g., to partially draw the first loop 650a into and out of the lumen 626 during actuation.

In addition, the fragmentor device 640 includes a fragmentor coil 642 including a first end 643 coupled to the catheter distal end 624, e.g., adjacent or within the lumen 626, and a second end 644 coupled to the guidewire 630, e.g., at hub 633. The fragmentor coil 642 may extend helically around the guidewire 630 between the first and second ends 632, 644, as best seen in FIG. 20B.

The fragmentor device 640 has two positions that it moves between during actuation. For example, FIG. 20A shows the fragmentor device 640 in a first or distal position in which the guidewire 630 is extended distally relative to the catheter distal end 624. Consequently, the fragmentor loops 650 and coil 644 are extended distally or longitudinally so that they adopt a low profile, e.g., with the coil 644 compressed around the guide wire 630 and the loops 650 lying substantially flat adjacent the guidewire 630. When the second handle portion 664 is actuated, the guidewire 630 is pulled proximally, thereby pulling the hub 633 on the distal end 634 and consequently compressing the fragmentor loops 650 and coil 644 proximally so that they adopt a larger profile, e.g., with the loops 650 adjacent one another and the coil 642 expanded away from the guidewire 630.

In the larger profile, the orientation of the loops 650 may approximate the diameter or other cross-section of a body lumen 90 within which the apparatus 610 is introduced, as best seen in FIG. 20B. To adjust the maximum diameter or cross-section of the loops 650 in the larger profile, the adjustment control 636 on the handle 660 may be adjusted, e.g., to shorten the guidewire 630 travel distance and reduce the maximum diameter, or to extend the guidewire 630 travel distance and increase the maximum diameter, as desired.

The distal end 634 of the core wire 630 may be substantially atraumatic, e.g., rounded or otherwise shaped to minimize risk of perforation and/or catching during advancement relative to the catheter distal end 624 within a patient's body.

Optionally, the distal end 634 may be covered by a coiled wire and/or a polymeric covering, and/or may include a "J" or other curved tip (not shown).

Optionally, the apparatus 610 may include one or more markers to facilitate positioning and/or advancement of the apparatus 610 during use. For example, one or more radiopaque markers may be placed on the catheter distal end 624, on the guidewire distal end 630, and/or on the fragmentor device 640. For example, one or more of the loops 650 and/or coil 642 may be formed from radiopaque or other materials that may facilitate imaging the apparatus 610 during use, similar to the previous embodiments.

Figure 21A:
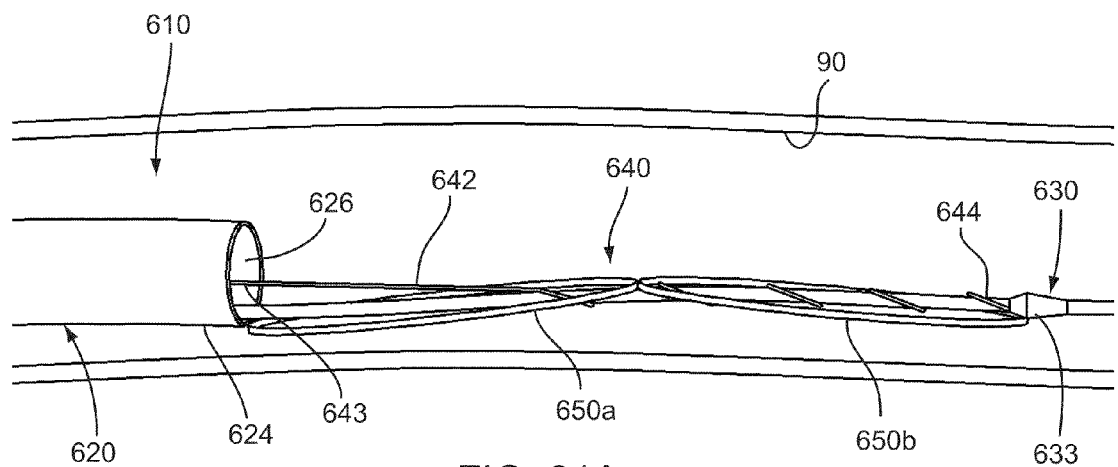
FIGS. 21A and 21B are details of a distal end of the apparatus of FIG. 19, showing lumen clearing elements being actuated between a low profile and a large profile, respectively.

Turning to FIGS. 21A-21F, an exemplary method for removing thrombus or other material 92 from within a body lumen 90 is shown. Initially, as shown in FIG. 21A, the apparatus 610 may be introduced into a patient's body and directed into a target body lumen 90. Similar to previous embodiments, the body lumen 90 may be a blood vessel, e.g., a vein or artery, a graft, e.g., an aorto-venous fistula, tubular xenograft, or synthetic tubular graft, and the like. The apparatus 610 may introduced from a percutaneous puncture or other entry site and advanced through any intervening body passages into the body lumen 90. Optionally, the apparatus 610 may be introduced through an introduced sheath, guide catheter, and the like (not shown). In addition or alternatively, the apparatus 610 may be advanced over a guidewire or other rail (not shown), e.g., if the catheter 620 or guidewire 630 includes a guidewire lumen (not shown).

As shown in FIG. 21A, the distal end 634 of the guidewire 630 has been directed through a mass of thrombus 92 such that the catheter distal end 624 is adjacent the thrombus 92 and the fragmentor device 640 at least partially contacts the thrombus 92. The fragmentor device 640 may be advanced along the thrombus 92 in the low profile, e.g., to reduce the risk of breaking off pieces of the thrombus 92 prematurely and/or pushing the thrombus 92 away from the catheter distal end 624.

Figure 21B:
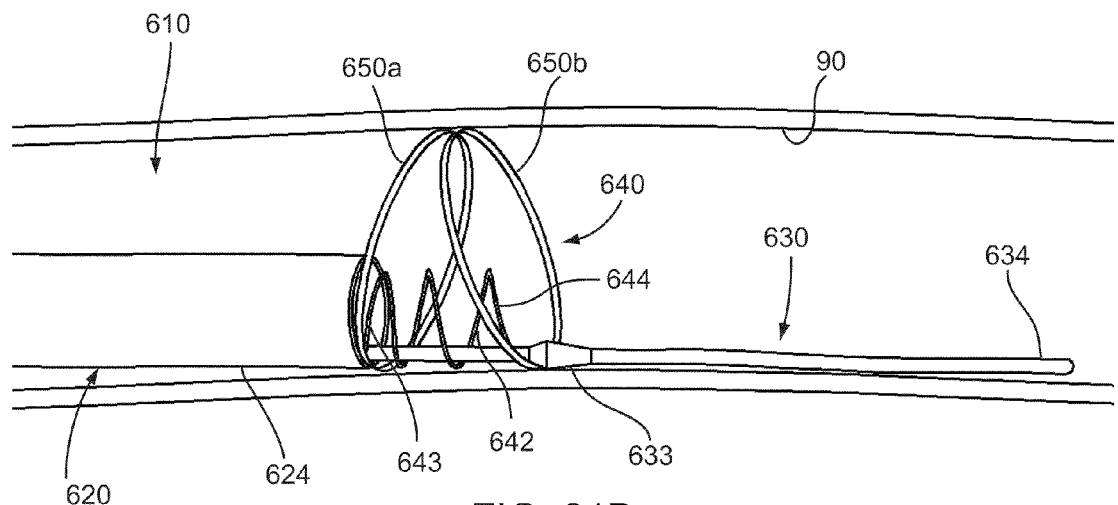
Figure 22A:
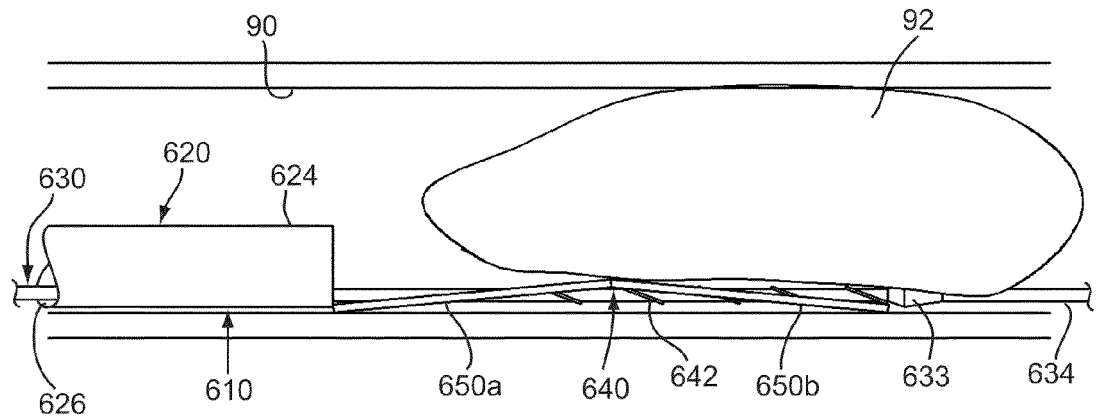
FIGS. 22A-22F are cross-sectional views of a body lumen, showing a method for removing obstructive material within the body lumen using the apparatus of FIGS. 18-21B.
Figure 22B:
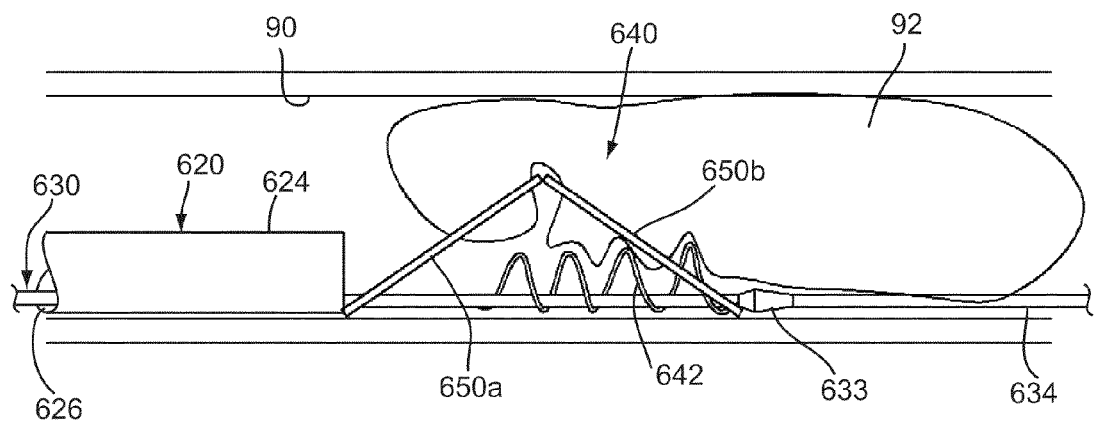
Figure 22C:
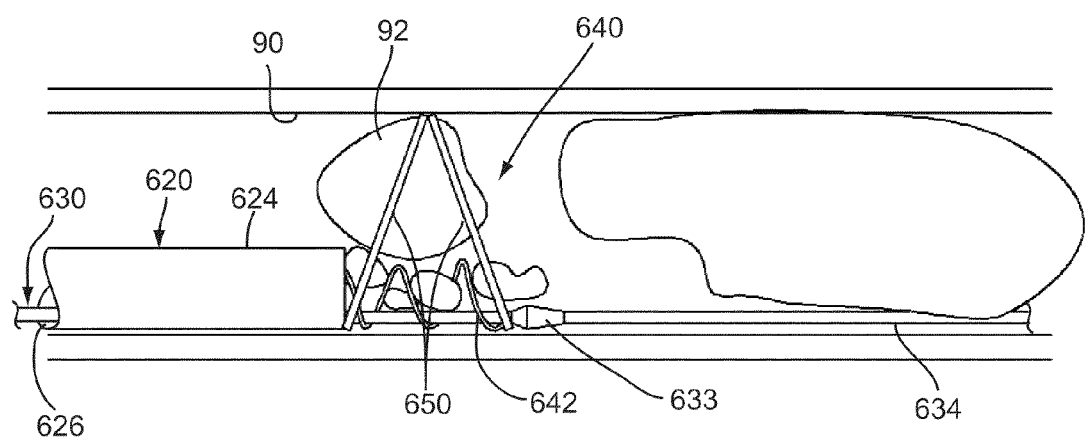
Figure 22D:
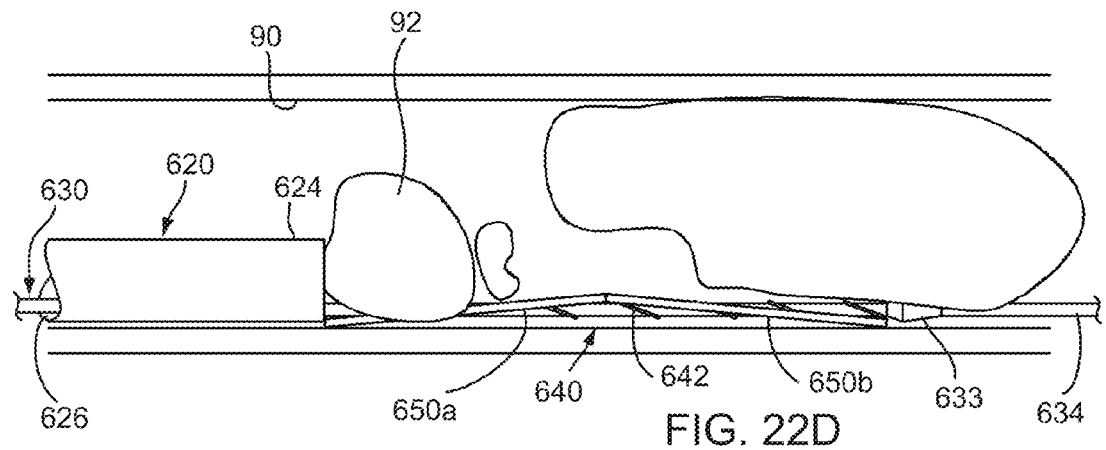
Figure 22E:
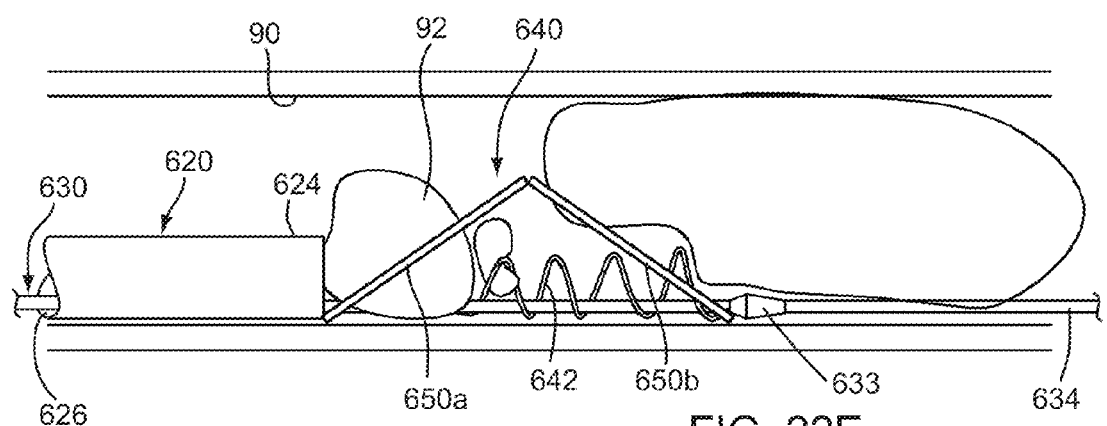
Figure 22F:
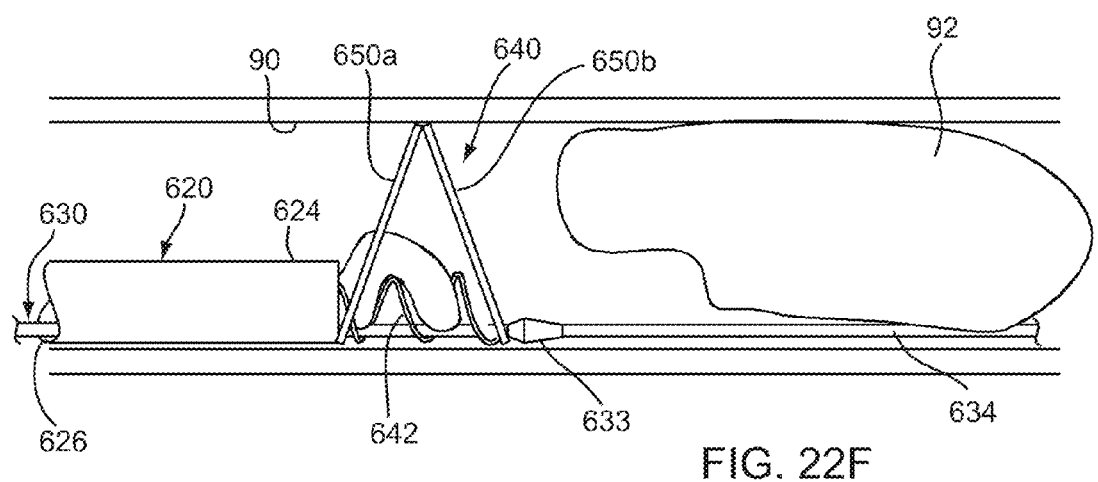

Turning to FIGS. 21B and 21C, the fragmentor device 640 is shown being actuated, e.g., such that the loops 650 expand from the low profile at least partially across the body lumen 90, and the coil 642 expands away from the guidewire 630, e.g., into the thrombus 92. As described above with reference to FIG. 20, to actuate the fragmentor device 640, the first and second handle portions 662, 664 may be squeezed together, e.g., pivoting the second handle portion 664 relative to the first handle portion 662 and pulling the proximal end 632 of the guidewire 630 proximally. This pulls the distal end of the guidewire 630, and consequently, the hub 633, loops 650, and coil 642 proximally, e.g., until the larger profile shown in FIG. 21C is achieved. This motion of the loops 650 and coil 642 may engage and cut or otherwise separate one or more pieces of the thrombus 92 from the main mass, as shown in FIG. 21C.

In addition, as the second handle portion 664 is actuated, the piston 669 may be drawn out of the chamber 670, thereby creating a vacuum to aspirate pieces of the thrombus 92 into the catheter lumen 626 and into the reservoir 672 (see FIG. 20). Alternatively, a syringe, external continuous source of vacuum, and the like (not shown) may be connected to the handle 660 to aspirate material into the catheter lumen 626, if desired, rather than using a self-contained apparatus 610, as shown. The separated pieces of thrombus 92 may be sufficiently small to enter freely into the catheter lumen 626 and/or sufficient suction may be created to pull pieces of the thrombus 92 into the catheter lumen 626.

Turning to FIG. 21D, actuation of the apparatus 610 may be released, e.g., by releasing the second handle portion 664. The handle 660 may include one or more springs or other biasing mechanisms (not shown) for automatically returning the second handle portion 664 to its original position, and consequently returning the fragmentor device 640 to the distal, low profile. Because all of the desired thrombus 92 may not have been removed, the user may again actuate the fragmentor device 640, e.g., as shown in FIGS. 21E and 21F, by again squeezing the handle 660 and causing the loops 650 and coil 643 to compress axially and expand radially to separate additional pieces of the thrombus 92 for aspiration into the catheter lumen 626. The process may be monitored using external imaging, e.g., fluoroscopy, ultrasound imaging, and the like, until it is confirmed that sufficient, e.g., substantially all of the, thrombus 92 has been broken up and aspirated. Optionally, a source of contrast (not shown) may be connected to the apparatus 610, e.g., that communicates with the catheter lumen 626 or a lumen in the guidewire 630, to inject contrast to facilitate imaging the thrombus 92 within the body lumen 90, similar to the previous embodiments. Once the body lumen 90 is sufficiently cleared, the apparatus 610 be directed to another body lumen or removed entirely from the patient's body.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for treating a body lumen, comprising:
   an elongate tubular member including a proximal end, a distal end sized for introduction into a body lumen, and a first lumen extending between the proximal and distal ends;
   an expandable balloon comprising a proximal end secured to the tubular member distal end, and a distal end comprising an outlet, the balloon comprising an interior communicating with the first lumen and the balloon outlet;
   an elongate member slidably disposed within the first lumen, the elongate member comprising a proximal end adjacent the tubular member proximal end, a distal end extending from the balloon outlet, and a guidewire lumen extending between the elongate member proximal and distal ends;
   a sealing member on the elongate member distal end distally beyond the balloon outlet, the elongate member being movable between a first distal position wherein the sealing member is spaced from the balloon outlet such that fluid introduced through the first lumen passes through the balloon interior and out the balloon outlet, and a second proximal position wherein the sealing member substantially seals the balloon outlet such that fluid introduced through the first lumen enters the balloon interior to expand the balloon;
   a helical member including a first end coupled to the tubular member distal end and a second end coupled to the elongate member distal end, the helical member extending helically around the elongate member within the balloon interior, the elongate member movable to a third position in which the elongate member distal end is directed towards the tubular member distal end to cause the helical member to expand radially outwardly to an expanded helical shape, thereby expanding the balloon to the expanded helical shape;

a stop secured to the elongate member within the balloon interior and secured to the helical member second end, the stop having a cross-section larger than the balloon outlet; and a handle on the tubular member proximal end and an actuator on the handle for directing the elongate member between the first distal and second proximal positions.

2. The apparatus of claim 1, wherein the sealing member has a cross-section larger than the balloon outlet.

3. The apparatus of claim 2, wherein the elongate member distal end has a cross-section smaller than the balloon outlet such that an annular lumen is defined between the elongate member and the balloon outlet for delivering fluid from the balloon interior through the balloon outlet when the elongate member is in the first distal position.

4. The apparatus of claim 1, wherein the elongate member has a cross-section smaller than the first lumen such that an annular lumen is defined between the elongate member and the tubular member for delivering fluid from the tubular member proximal end into the balloon interior.

5. The apparatus of claim 1, wherein the stop limits relative movement of the balloon distal end relative to the elongate member distal end as the elongate member is directed between the second proximal and third positions.

6. The apparatus of claim 1, further comprising a source of vacuum communicating with the first lumen for collapsing the balloon before the elongate member is directed to the third position such that the balloon conforms substantially to the expanded helical shape of the helical member.

7. The apparatus of claim 1, wherein the balloon distal end is directed towards the balloon proximal end when the elongate member is moved to the third position, thereby axially compressing the balloon.

8. The apparatus of claim 7, wherein the elongate member is movable from the third position back towards the second proximal position, thereby extending and collapsing the helical member, the stop engaging the balloon distal end and directing the balloon distal end distally as the elongate member is moved from the third position back towards the second proximal position, thereby axially extending and collapsing the balloon.

9. The apparatus of claim 1, wherein the balloon comprises elastic material.

10. The apparatus of claim 1, wherein the balloon comprises substantially inelastic material.

11. The apparatus of claim 1, wherein the elongate member is biased to one of the first distal and second proximal positions.

12. The apparatus of claim 1, wherein the handle comprises a slot, and wherein the actuator comprises a push button slidable axially within the slot to direct the elongate member between the first distal, second proximal, and third positions.

13. The apparatus of claim 12, wherein the slot comprises one or more pockets or detents that may capture the push button to releasably secure the push button, and consequently the elongate member, in one or more of the first distal, second proximal, and third positions.

14. An apparatus for treating a body lumen, comprising:

an outer tubular member including a proximal end, a distal end sized for introduction into a body lumen, and a first lumen extending between the proximal and distal ends;

an expandable balloon comprising a proximal end secured to the outer member distal end, and a distal end comprising an outlet, the balloon comprising an interior communicating with the first lumen and the balloon outlet;

an inner member slidably disposed within the first lumen and having a cross-section smaller than the first lumen such that an annular lumen is defined between the outer and inner members between the proximal and distal ends of the outer member, the inner member comprising a proximal end adjacent the outer member proximal end, and a distal end extending from the balloon outlet;

a sealing member on the inner member distal end distally beyond the balloon outlet, the inner member movable between a first distal position wherein the sealing member is spaced from the balloon outlet such that fluid introduced through the first lumen passes through the balloon interior and out the balloon outlet, and a second proximal position wherein the sealing member substantially seals the balloon outlet such that fluid introduced through the first lumen enters the balloon interior to expand the balloon;

a helical member comprising a first end coupled to the outer member distal end and a second end coupled to the inner member distal end, the helical member extending helically around the inner member within the balloon interior, the inner member movable to a third position in which the inner member distal end is directed towards the outer member distal end to cause the helical member to expand radially outwardly, thereby expanding the balloon to an expanded helical shape; and a stop on the inner member distal end spaced proximally from the sealing member and secured to the second end of the helical member, the stop having a cross-section larger than the balloon outlet.

15. The apparatus of claim 14, wherein the stop limits relative movement of the balloon distal end relative to the inner member distal end as the inner member is directed between the second proximal and third positions.

16. The apparatus of claim 14, further comprising a source of vacuum communicating with the first lumen for collapsing the balloon before the inner member is directed to the third position such that the balloon conforms substantially to the shape of the helical member as the balloon is expanded to the expanded helical shape.

17. The apparatus of claim 14, wherein the inner member comprises a guidewire lumen extending between the inner member proximal and distal ends.

18. The apparatus of claim 14, wherein the balloon comprises substantially inelastic material.

19. The apparatus of claim 14, further comprising a handle on the tubular member proximal end, and an actuator on the handle for directing the inner member between the first distal and second proximal positions.

20. The apparatus of claim 19, wherein the handle comprises a slot, and wherein the actuator comprises a push button slidable axially within the slot to direct the inner member between the first distal, second proximal, and third positions.

* * * * *